United States Patent
Levy

(10) Patent No.: US 12,116,611 B2
(45) Date of Patent: Oct. 15, 2024

(54) METHOD OF TREATING INTELLECTUAL DISABILITY, AUTISM AND EPILEPSY ASSOCIATED WITH AN IQSEC2 MUTATION AND FOR IDENTIFYING MEDICAMENTS FOR TREATING THE SAME

(71) Applicant: TECHNION RESEARCH & DEVELOPMENT FOUNDATION LIMITED, Haifa (IL)

(72) Inventor: Andrew Levy, Haifa (IL)

(73) Assignee: TECHNION RESEARCH & DEVELOPMENT FOUNDATION LIMITED, Haifa (IL)

(*) Notice: Subject to any disclaimer, the term of this patent is extended or adjusted under 35 U.S.C. 154(b) by 1101 days.

(21) Appl. No.: 16/965,100

(22) PCT Filed: Jan. 27, 2019

(86) PCT No.: PCT/IL2019/050106
§ 371 (c)(1),
(2) Date: Jul. 27, 2020

(87) PCT Pub. No.: WO2019/145957
PCT Pub. Date: Aug. 1, 2019

(65) Prior Publication Data
US 2021/0032673 A1    Feb. 4, 2021

Related U.S. Application Data

(60) Provisional application No. 62/622,912, filed on Jan. 28, 2018.

(51) Int. Cl.
| | |
|---|---|
| *C12Q 1/02* | (2006.01) |
| *A01K 67/0278* | (2024.01) |
| *A61K 31/381* | (2006.01) |
| *A61P 25/28* | (2006.01) |
| *C12N 5/074* | (2010.01) |

(52) U.S. Cl.
CPC .......... *C12Q 1/025* (2013.01); *A01K 67/0278* (2013.01); *A61K 31/381* (2013.01); *A61P 25/28* (2018.01); *C12N 5/0696* (2013.01); *A01K 2217/072* (2013.01); *A01K 2227/105* (2013.01); *A01K 2267/0356* (2013.01)

(58) Field of Classification Search
CPC ................ C12Q 1/025; A01K 67/0278; A01K 2217/072; A01K 2267/0356; A01K 2227/105; C12N 5/0696; A61P 25/28; A61K 31/381
See application file for complete search history.

(56) References Cited

U.S. PATENT DOCUMENTS

2015/0119327 A1    4/2015    Muotri et al.

FOREIGN PATENT DOCUMENTS

| | | |
|---|---|---|
| EP | 1687427 | 8/2006 |
| KR | 20140104450 A | 8/2014 |

OTHER PUBLICATIONS

Darville, H et al. Human Pluripotent Stem Cell-derived Cortical Neurons for High Throughput Medication Screening in Autism: A Proof of Concept Study in SHANK3 Haploinsufficiency Syndrome. EBioMedicine. Jul. 2016;9:293-305 (Year: 2016).*
Gould TD, et al. Involvement of AMPA receptors in the antidepressant-like effects of lithium in the mouse tail suspension test and forced swim test. Neuropharmacology. Mar. 2008;54(3):577-87 (Year: 2008).*
Simmons et al (Neurobiol Dis. Feb. 2011;41(2):436-44) (Year: 2011).*
Wink et al (Expert Opinion on Emerging Drugs, (2010) 15:3, 481-494) (Year: 2010).*
Yang et al (Current Pharmaceutical Design, 2014, 20, 5186-5193) (Year: 2014).*
Hinze et al (2017) Incorrect dosage of IQSEC2, a known intellectual disability and epilepsy gene, disrupts dendritic spine morphogenesis. Translational psychiatry, 7.5: e1110.
Myers et al (2013) Arf6-GEF BRAG1 regulates JNK-mediated synaptic removal of GluA1-containing AMPA receptors: a new mechanism for nonsyndromic X-linked mental disorder. Journal of Neuroscience, 32.34: 11716-11726.
Levy et al (2019) IQSEC2-Associated Intellectual Disability and Autism, International Journal of Molecular Sciences 20, 3038, doi: 10:3390.
Rogers et al (2019) An IQSEC2 Mutation Associated With Intellectual Disability and Autism Results in Decreased Surface AMPA Receptors, Frontiers in Molecular Neuroscience, vol. 12, Article 43.
Zipper et al (2017) Development Progression of intellectual disability, autism, and epilepsy in a child with an IQSEC2 gene mutation, Clinical Case Reports 5(10): 1639-1643.

(Continued)

*Primary Examiner* — Adam Weidner
*Assistant Examiner* — Georgiana C Reglas
(74) *Attorney, Agent, or Firm* — The Roy Gross Law Firm, LLC; Roy Gross

(57) ABSTRACT

The invention provides a method of screening for a potential candidate for treating autism, epilepsy and/or intellectual disability in a subject in need comprising contacting a cell culture or an animal with the potential drug and detecting one or more of the following features: enhancing with the binding of apocalmodulin to the IQ domain of IQSEC2; reducing the production of ARF6-GTP; inhibiting the constitutive activation of guanine nucleotide exchange factor (GEF) IQSEC2; increasing the surface expression of AMPA receptors the brain or a cell; and/or increasing basal synaptic transmission in the brain or the cell. Further provided is a method of treating autism, epilepsy and/or intellectual disability in a subject in need by administering a drug capable of presenting one or more of the above identified features in the described cell and animal models.

4 Claims, 13 Drawing Sheets

Specification includes a Sequence Listing.

(56) References Cited

OTHER PUBLICATIONS

International Search Report for PCT/IL2019/050106 Completed May 8, 2019; Mailed May 8, 2019 3 Pages.
Written Opinion for PCT/IL2019/050106 Completed May 8, 2019; Mailed May 8, 2019 7 Pages.

* cited by examiner

METHOD OF TREATING INTELLECTUAL DISABILITY, AUTISM AND EPILEPSY ASSOCIATED WITH AN IQSEC2 MUTATION AND FOR IDENTIFYING MEDICAMENTS FOR TREATING THE SAME

CROSS REFERENCE TO RELATED APPLICATIONS

This application is a National Phase of PCT Patent Application No. PCT/IL2019/050106 having International filing date of Jan. 27, 2019, which claims the benefit of priority of U.S. Provisional Application No. 62/622,912 filed on Jan. 28, 2018. The contents of the above applications are all incorporated by reference as if fully set forth herein in their entirety.

FIELD OF THE INVENTION

The invention is directed to methods for treating intellectual disability, autism and epilepsy associated with an IQSEC2 mutation and to method and animal and cell models for screening for medicaments for treating autism and epilepsy associated with an IQSEC2 mutation.

BACKGROUND OF THE INVENTION

IQSEC2 is an X-linked gene which has been previously associated with intellectual disability (ID), autism and epilepsy (Shoubridge et al, 2010; Zerem et al, 2016; Fieremans et al, 2015; Alexander-Bloch et al, 2016; Kalscheuer et al, 2016; Mignot and Depienne, 2018; Shoubridge et al, 2019) with mutations in IQSEC2 accounting for approximately 2% of patients with ID and epilepsy referred for exome sequencing (Heyne et al, 2018).

The IQSEC2 protein is localized in excitatory synapses as part of the NMDA receptor complex via interaction with postsynaptic density proteins DLG1, DLG2 and DLG4 and has been proposed to play a role in synaptic plasticity and dendritic spine formation (Murphy et al, 2006; Sakagami et al, 2008; Hinze et al, 2017). Biochemically IQSEC2 is a member of the GEF (guanine nucleotide exchange factor) family of proteins whose role is to promote exchange of GDP for GTP on specific Arfs (ADP ribosylation factors) and thereby activate the Arf. The target Arf for IQSEC2 is not known but binding of IQSEC2 to Arf6 has been demonstrated in vitro (Sakagami et al, 2008). Arf6, similar to other Arfs, regulates actin dynamics in dendritic spines and membrane trafficking, and is the only Arf which regulates trafficking between the cell surface membrane and endocytotic membranes (Jaworski, 2007; Donaldson et al, 2003; Choi et al 2006). The GEF activity of IQSEC2, mediated through ARF6, has recently been demonstrated to be required for the activity dependent removal of α-amino-3-hydroxyl-5-methyl-4-isoxazolepropionic acid (AMPA) receptors (Brown et al 2017; Petersen et al 2018) from the surface of hippocampal neurons. The regulation of surface synaptic AMPA receptors has been shown to be critically involved in learning and memory processes with alterations in AMPA trafficking being associated with cognitive impairment and social behavioral abnormalities (Parkinson and Hanley, 2018; Medin et al, 2018; Awasthi et al, 2018). Demonstration that IQSEC2 can regulate AMPA trafficking may therefore provide a mechanistic link for the severe intellectual disability and abnormalities in social behavior associated with mutations in IQSEC2.

The IQSEC2 gene contains 15 exons and codes for a protein of 1488 amino acids (long isoform) with 98.5% homology between murine IQSEC2 and human IQSEC2. The coding sequence contains several canonical domains notably a catalytic domain (SEC7) [aa 746-939] characteristic of all GEFs promoting GTP exchange and an IQ like domain [aa 347-376] which has been suggested to bind calmodulin and thereby modulate the GEF activity of IQSEC2 (Shoubridge et al, 2010).

At least 70 different mutations have been described in the IQSEC2 gene all associated with moderate to severe intellectual disability, with variable seizures and autistic traits (Shoubridge et al, 2019). The genotype-phenotype relationship for these mutations is not understood. Many of these mutations cluster in recognized functional domains of IQSEC2 such as the Sec7 and IQ domains thereby providing a possible mechanism by which they produce disease (Mignot and Depienne, 2018; Shoubridge et al, 2019). There have been no reports in animal models on how altered IQSEC2 function for any of these mutations may influence cognition or social behavior.

There is a need to understand the molecular pathophysiology of IQSEC2 mutations for a personalized treatment program to provide much-needed hope and help to affected children and their families.

SUMMARY OF THE INVENTION

It was recently described an A350V mutation in IQSEC2 associated with intellectual disability, autism and epilepsy. Understanding the molecular pathophysiology of this mutation is important for developing targets for drug intervention. The findings described here show that the A350V mutation results in interference with the binding of apocalmodulin to the IQ domain of IQSEC2. Further, it is demonstrated here that this mutation results in constitutive activation of the guanine nucleotide exchange factor (GEF) activity of IQSEC2 resulting in increased production of the active form of Arf6. In a CRISPR generated mouse model of the A350V IQSEC2 mutation, it is demonstrated here that the surface expression of GluA2 AMPA receptors in mouse hippocampal tissue was significantly reduced in A350V IQSEC2 mutant mice compared to wild type IQSEC2 mice and that there is a significant reduction in basal synaptic transmission in the hippocampus of A350V IQSEC2 mice compared to wild type IQSEC2 mice. Finally, the A350V IQSEC2 mice demonstrated increased activity, abnormal social behavior and learning as compared to wild type IQSEC2 mice. These findings suggest a model of how the A350V mutation in IQSEC2 may mediate disease with implications for targets for drug therapy. These studies provide a paradigm for a personalized approach to precision therapy for a disease that heretofore has no therapy.

In an embodiment of the invention, there is provided a method of treating autism, epilepsy and/or intellectual disability in a subject in need, which is typically a child, comprising administering to the subject in need a medicament that is capable of: enhancing the binding of apocalmodulin to the IQ domain of IQSEC2; reducing the production of ARF6-GTP; inhibiting the constitutive activation of guanine nucleotide exchange factor (GEF) IQSEC2; increasing the surface expression of AMPA receptors the brain or a cell; and/or increasing basal synaptic transmission in the brain. In some embodiments of the invention, the increasing of the surface expression of AMPA receptors in the brain is in the hippocampus. In some embodiments of the invention, the AMPA receptors are GluA2 AMPA receptors.

In some embodiments of the invention, the autism, epilepsy and/or intellectual disability are associated with a mutation in the IQ domain of IQSEC2. In some embodiments of the invention, the mutation in the IQ domain of IQSEC2 is an A350V mutation. In some embodiments of the invention, the one or more of: enhancing the binding of apocalmodulin to the IQ domain of IQSEC2; reducing the production of ARF6-GTP; inhibiting the constitutive activation of guanine nucleotide exchange factor (GEF) IQSEC2; increasing the surface expression of AMPA receptors in the brain or the cell; and/or increasing basal synaptic transmission in the brain or the cell, are previously detected in a cell culture model or in an animal model.

In some embodiments of the invention, the cell culture model or the animal model are based on an A350V mutation in the IQ domain of IQSEC2. The animal model may be in some embodiments, a CRISPR murine model.

In some embodiments of the invention, there is provided a method of screening for a potential candidate for treating autism, epilepsy and/or intellectual disability in a subject in need comprising contacting a cell culture or an animal with the potential drug and detecting one or more of the following features:

enhancing with the binding of apocalmodulin to the IQ domain of IQSEC2;
reducing the production of ARF6-GTP;
inhibiting the constitutive activation of guanine nucleotide exchange factor (GEF) IQSEC2;
increasing the surface expression of AMPA receptors the brain or a cell; and/or
increasing basal synaptic transmission in the brain or the cell, wherein if the potential candidate is:

enhancing the binding of apocalmodulin to the IQ domain of IQSEC2;
reducing the production of ARF6-GTP;
inhibiting the constitutive activation of guanine nucleotide exchange factor (GEF) IQSEC2;
increasing the surface expression of AMPA receptors the brain or the cell; and/or
increasing basal synaptic transmission in the brain or the cell, then the potential drug is suitable for treating autism, epilepsy and/or intellectual disability in a subject.

In some embodiments of the invention, the increasing the surface expression of AMPA receptors the brain is in the hippocampal tissue.

In some embodiments of the invention, the AMPA receptors in the brain are GluA2 AMPA receptors.

In some embodiments of the invention, the autism, epilepsy or intellectual disability are associated with a mutation in the IQSEC2 gene. In some embodiments of the invention, the autism, epilepsy or intellectual disability are associated with a mutation in the IQ domain of IQSEC2.

In some embodiments of the invention, the mutation in the IQ domain of IQSEC2 is an A350V mutation.

In some embodiments of the invention, the cell culture model or the animal model, which can be for example a CRISPR murine model are based on an A350V mutation in the IQ domain of IQSEC2.

In some embodiments of the invention, the cell culture model is derived from a subject having a mutation in the IQ domain of IQSEC2 and may be in some embodiments, an induced pluripotent stem cells (IPS).

In some embodiments of the invention, the autism is at least one of non-syndromic autism, classical autism, Asperger's syndrome, Rett's syndrome, childhood disintegrative disorder, or pervasive developmental disorder not otherwise specified (PDD-NOS).

BRIEF DESCRIPTION OF THE DRAWINGS

FIG. 1 A-C demonstrate the functional domain organization of the IQSEC2 gene and amino acid sequence of IQSEC2 IQ motif mutants used in this study.

FIGS. 2 A-B show the binding of wild type and mutant IQSEC2 to calmodulins in cells using the Lumier assay.

Representative images of immunoblots after BS3-crosslinking of samples to assess surface (crosslinking "+") and total protein expression of AMPA receptors (crosslinking "–"). Actin was used for normalization.

Quantification of relative total protein levels of AMPA receptor subunits in samples not crosslinked. Signal intensities normalized to actin signal and wild type as 100%.

Quantification of total sum of all AMPA receptor subunits in samples not crosslinked.

Quantification of AMPA receptor subunit percentage composition in samples not crosslinked.

Quantification of relative surface protein levels of AMPA receptor subunits in samples treated with BS3 (crosslinking "+"). Surface protein indicated by "s" on the blots in A. Signal intensities of the bands at 250 kDa and above were normalized to actin signal and wild type as 100%.

Quantification of total sum of all AMPA receptor subunits at the membrane surface.

Quantification of surface AMPA receptor subunit percentage composition (significant differences in GluA2 composition).

Optical densitometry quantification values represent the mean SEM (n=4-5, *p<0.05, n.s. p>0.05, t-test, two-tailed).

Figure 7A:
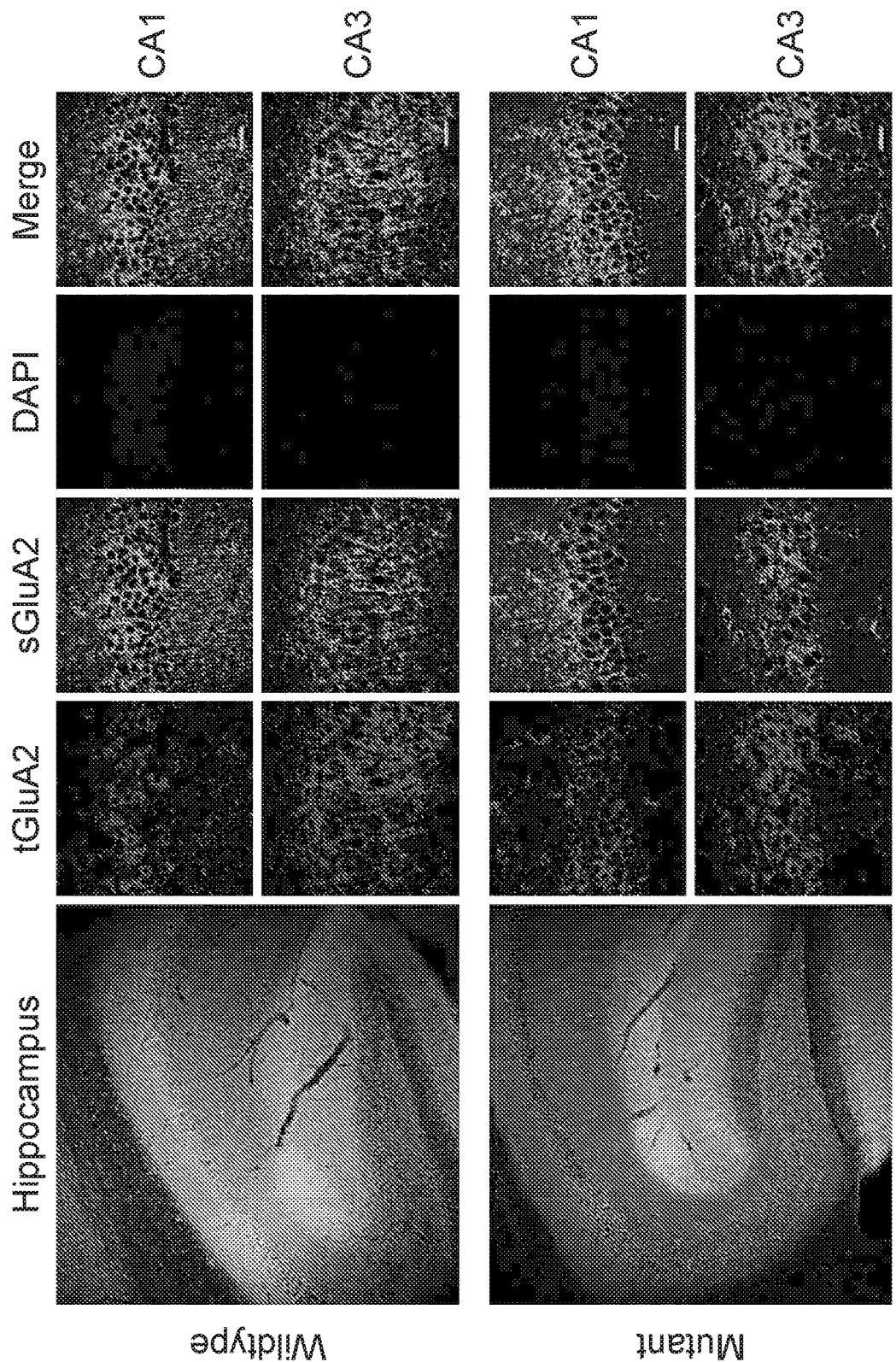
Figure 7B:
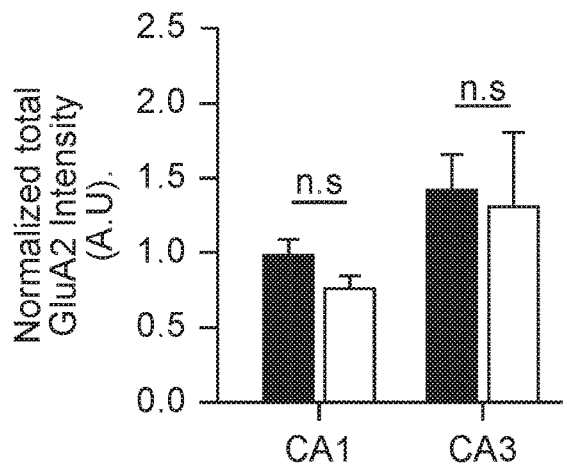
Figure 7C:
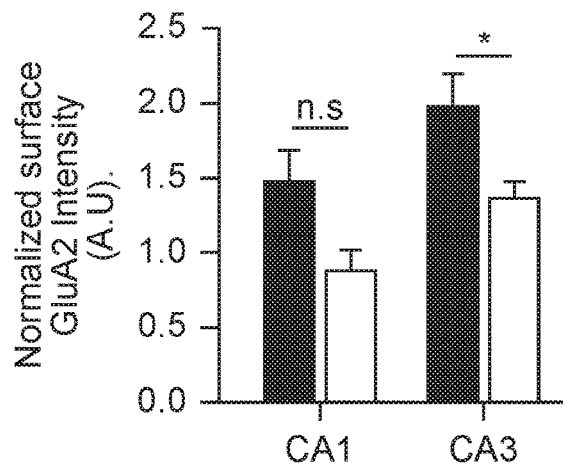

FIGS. 7A-7C show the assessment of surface expression of AMPA receptor GluA2 in hippocampus by immunocytochemistry.

Representative images of immunohistochemistry of total (tGluA2) and surface (sGluA2) AMPA receptor GluA2 in wildtype and A350V IQSEC2 mutant hippocampi. Higher power representative images of the CA1 and CA3 regions are shown (right panel). Labeled scale bar for high-resolution images=20 μm.

Quantification of the normalized total GluA2 levels. Data represent mean SEM, n=5 male mice in each group. No significant difference (n.s) p>0.05, t-test, two-tailed).

Quantification of the normalized levels of surface GluA2 expression. Data represent mean SEM, n=5 male mice in each group, *p<0.05, n.s. p>0.05, t-test, two-tailed).

Figure 8:
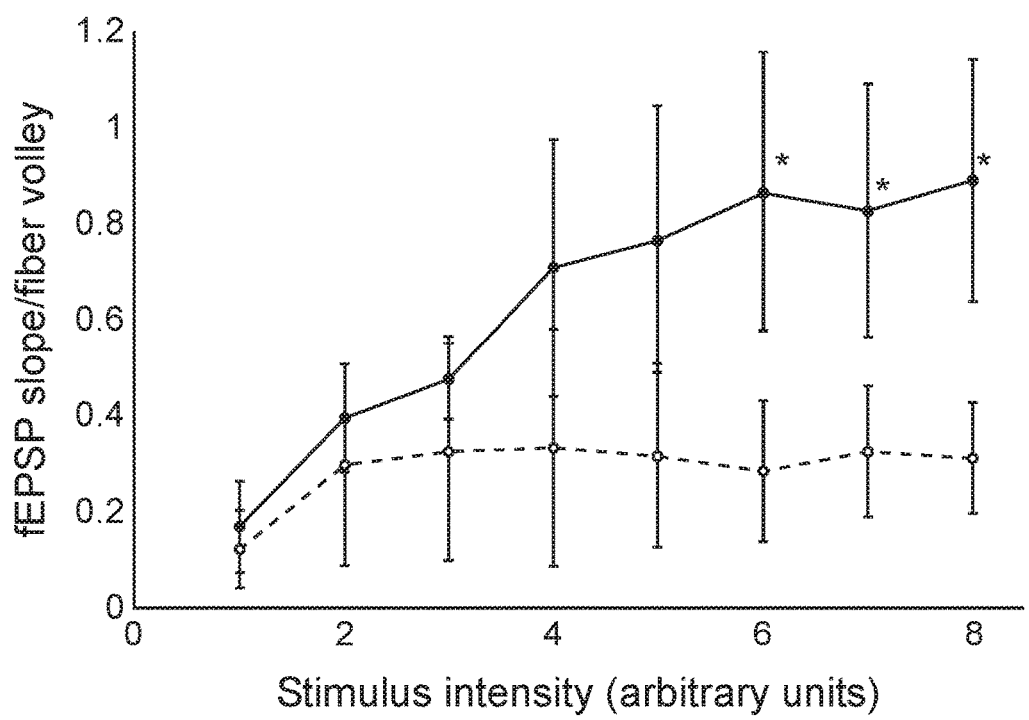

FIG. 8 shows the assessment of basal synaptic transmission in CA1 region of hippocampus Input/output curves representing synaptic responses (fEPSP slope/fiber volley) resulting from different stimulus intensities. Stimulus intensity numbers are arbitrary units; where 1 is intensity that gives minimum response and 8 is intensity that produces maximum response. Synaptic responses were significantly lower in A350V IQSEC2 mice (orange) compared to WT IQSEC2 mice (blue) where indicated with *

FIG. 9 A-E shows the behavioral phenotype of A350V IQSEC2 mouse model.

Figure 9A:
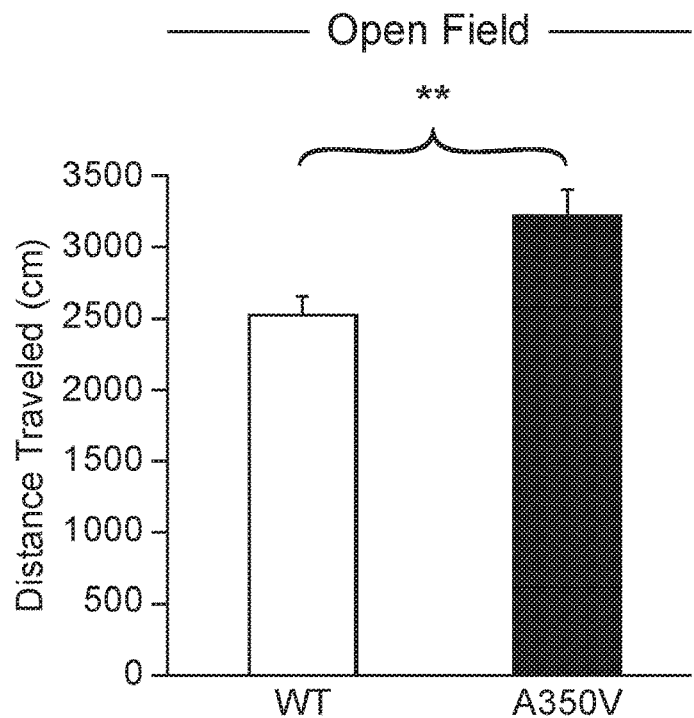

FIG. 9A shows that A350V display increased locomotion activity in an open field test (n=13 wild type and A350V IQSEC2 mice.

Figure 9B:
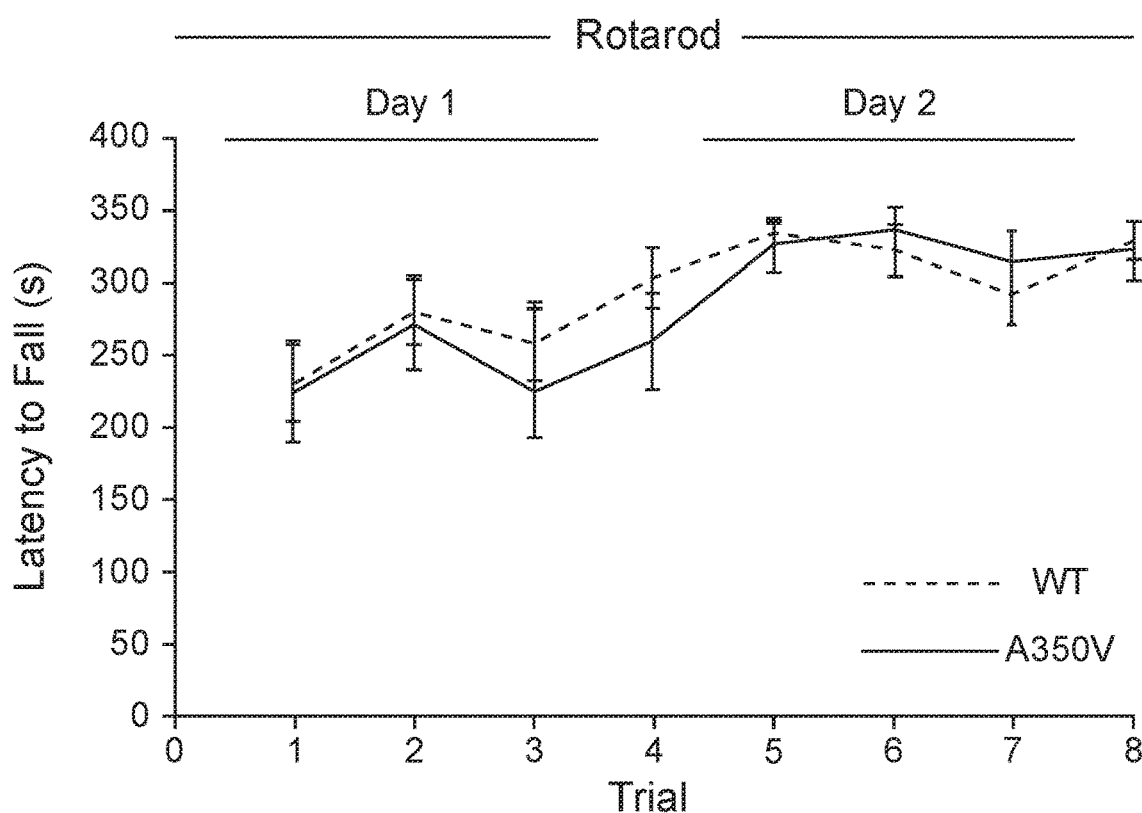

FIG. 9B shows the intact motor coordination in A350V relative to WT tested by the Rotarod test expressed as an equivalent learning curve and retention across two days in the two groups (n=13 wild type and A350V IQSEC2 mice).

Figures 9C, 9D, 9E:
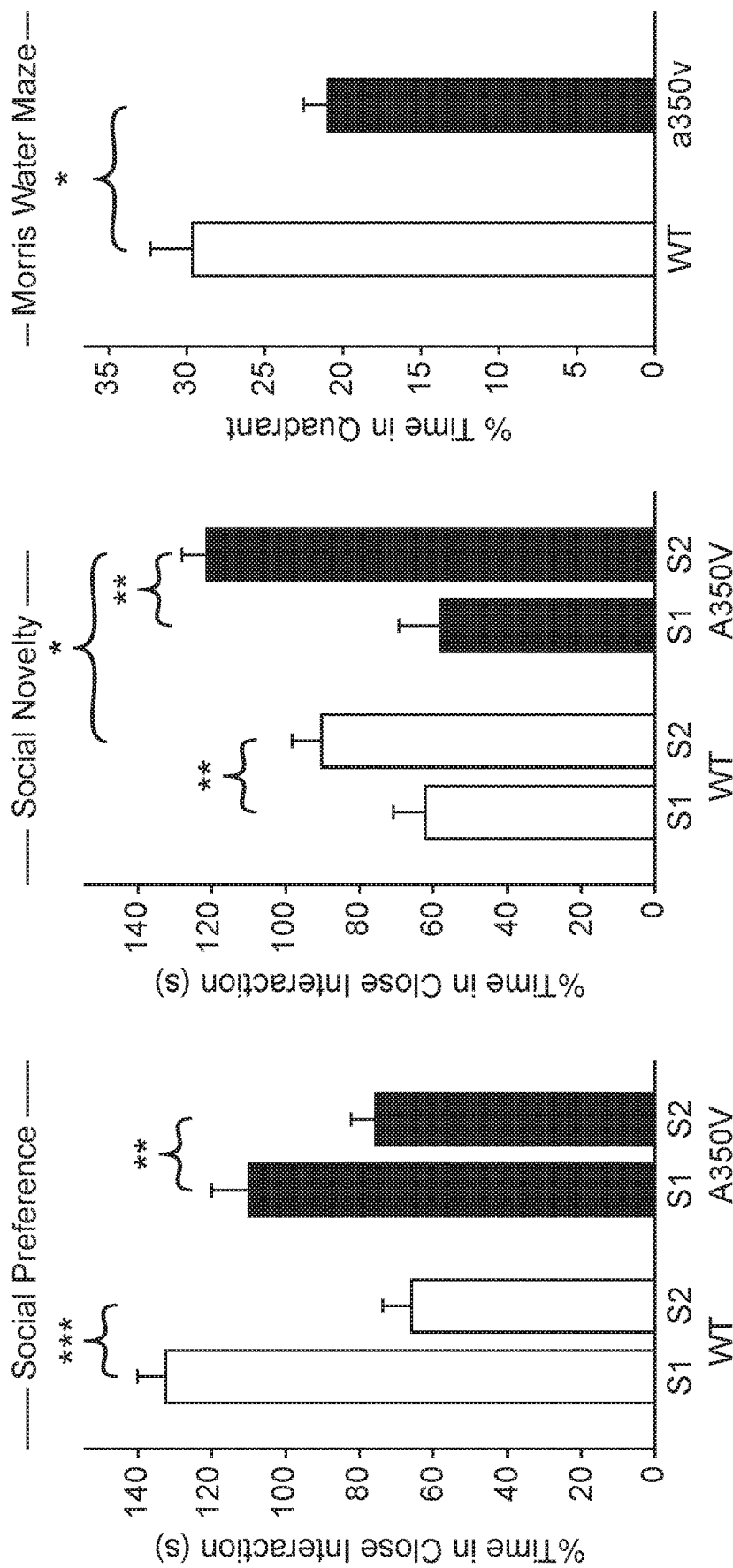

FIG. 9C shows the duration of time spent in close interaction with Stranger 1 (S1) and an object (O) in the three-chamber social preference test demonstrating both A350V and WT preferred interacting with S1 although this preference was less pronounced in A350V (n=13 wild type and A350V IQSEC2 mice).

FIG. 9D shows the preference for social novelty expressed as the duration of time spent in close interaction with a previously encountered stranger animal (S1) relative to a novel stranger animal (S2) revealed a tendency to spend more time with S2 in WT and A350V, with significant enhancement of this preference for social novelty in A350V mice (n=12 wild type and 9 A350V IQSEC2 mice).

FIG. 9E shows the learning and memory deficits in A350V mice shown by the percentage time spent in the target quadrant in a Morris water maze test (n=5 wild type and A350V IQSEC2 mice).

Data indicate means±SEM. *p<0.05, p<0.01, *p<0.001.

Figure 10:
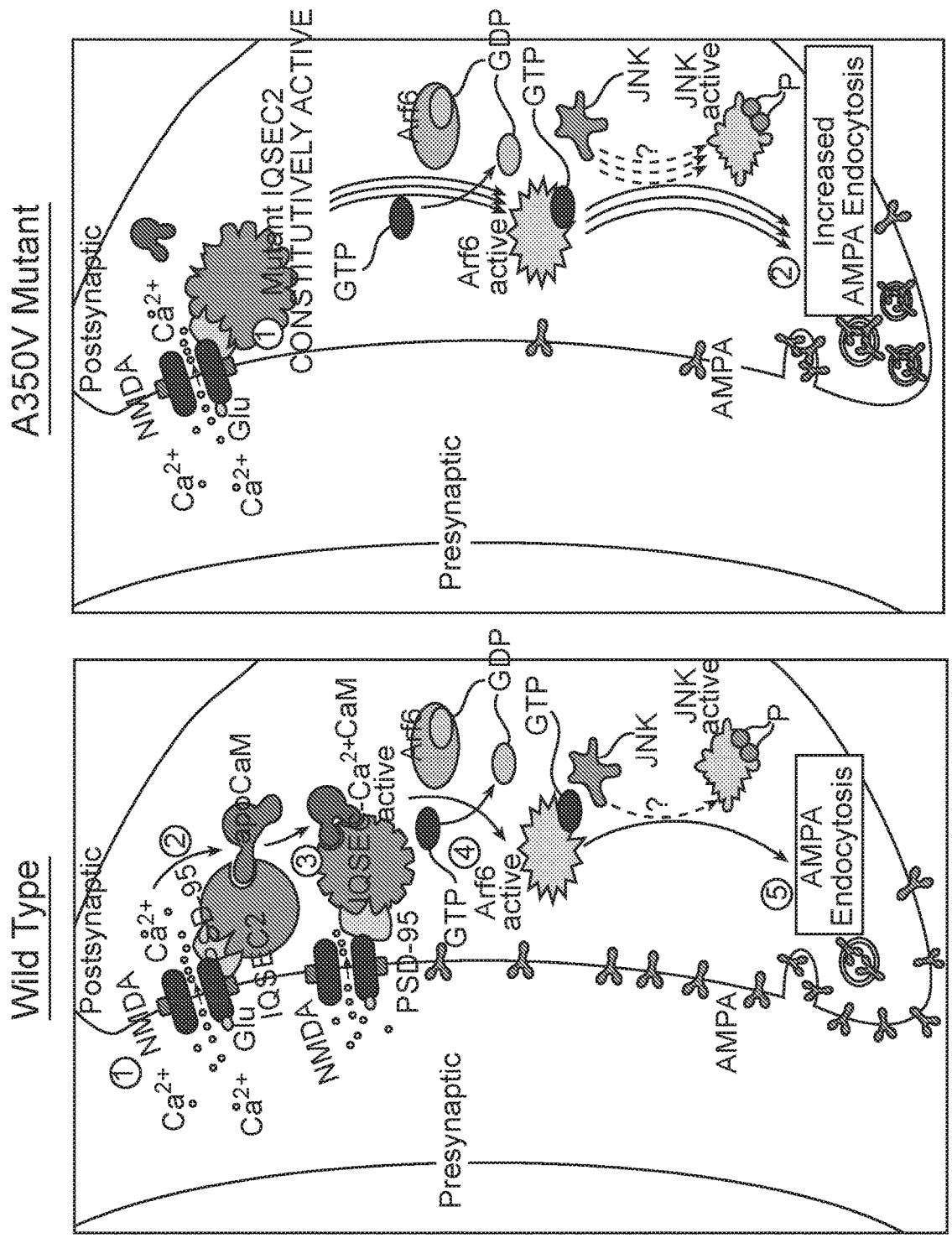

FIG. 10 is a schematic model of regulatory cascade mediated by wild type and A350V IQSEC2 mutant and consequences for AMPA trafficking.

Wild type IQSEC2. (1) Activation of NMDA receptor with calcium influx. (2) Calcium can bind to apocalmodulin which is already bound to IQSEC2. (3) Ca-calmodulin bound to IQSEC2 induces a conformational change in IQSEC2 that leads to activation of IQSEC2 GEF activity (4) resulting in formation of active Arf6-GTP. Arf6-GTP promotes endocytosis of surface AMPA receptors (5) by pathways that are poorly understood, but which may include JNK (Myers et al, 2012).

A350V mutant IQSEC2. (1) A350V IQSEC2 has conformation similar to active form of wild type IQSEC2 and has constitutive GEF activity capable of promoting increased Arf6-GTP formation (2). Increased Arf6-GTP results in more pronounced down regulation of surface AMPA receptors (3).

DETAILED DESCRIPTION OF THE EMBODIMENTS OF THE INVENTION

ID and associated disorders in a child resulting from a de novo mutation identified by exome sequencing in the IQSEC2 gene (A350V, i.e. valine for alanine substitution in amino acid residue 350) was recently reported (Zipper et al, 2017). In one embodiment, this invention is based on the molecular mechanisms underlying the pathophysiology of IQSEC2 mutation in vitro and in a CRISPR murine model with the goal of developing precise therapies to alleviate at least in part the severe clinical syndrome associated with the mutation. In another embodiment, this invention is based on the molecular mechanisms underlying the pathophysiology of the A350V IQSEC2 mutation in vitro and in a CRISPR murine model with the goal of developing precise therapies to alleviate at least in part the severe clinical syndrome associated with the mutation. First, as the A350V mutation is in the IQ calmodulin binding domain of IQSEC2, experiments were done to define how this mutation may affect the interaction of IQSEC2 with calmodulin. Second, as other mutations in the IQ domain have been associated with changes in the ability of IQSEC2 to promote GTP exchange on Arf6 in response to calcium (Shoubridge et al 2010; Myers et al, 2012) it was investigated whether the A350V mutation may also alter Arf6 activity and whether this regulation was sensitive to calcium. Third, as IQSEC2 induced activation of Arf6 has been shown to modulate AMPA receptor trafficking (Brown et al, 2016) there was a question as to how the A350V mutation may affect this trafficking in a CRISPR model and specifically surface AMPA receptors which have been linked to learning and memory (Parkinson et al, 2018). Fourth, experiments were done to determine how the A350V mutation may affect basal hippocampal synaptic transmission. Finally, in an attempt to recapitulate the clinical phenotype in the CRISPR model assessed the effects of the A350V IQSEC2 mutation on behavioral phenotypes focusing on tests assessing locomotion, social interactions and learning were assessed.

Intellectual disability (or ID) is a term used when a person has certain limitations in cognitive functioning and skills, including communication, social and self-care skills. These limitations can cause a child to develop and learn more slowly or differently than a typically developing child. Intellectual disability can happen any time before a child turns 18 years old, even before birth. Intellectual disability is the most common developmental disability. According to the American Association of Intellectual and Developmental Disabilities, an individual has intellectual disability if he or she meets three criteria: IQ is below 70-75; There are significant limitations in two or more adaptive areas (skills that are needed to live, work, and play in the community, such as communication or self-care) and the condition manifests itself before the age of 18.

In an embodiment of the invention, there is provided a method of treating autism, epilepsy and/or intellectual disability in a subject in need, which is typically a child, comprising administering to the subject in need a medicament that is capable of: enhancing the binding of apocalmodulin to the IQ domain of IQSEC2; reducing the production of ARF6-GTP; inhibiting the constitutive activation of guanine nucleotide exchange factor (GEF) IQSEC2; increasing the surface expression of AMPA receptors the brain or a cell; and/or increasing basal synaptic transmission in the brain. In some embodiments of the invention, the increasing of the surface expression of AMPA receptors in the brain is in the hippocampus. In some embodiments of the invention, the AMPA receptors are GluA2 AMPA receptors.

In some embodiments of the invention, the autism, epilepsy and/or intellectual disability are associated with a mutation in the IQ domain of IQSEC2. In some embodiments of the invention, the mutation in the IQ domain of IQSEC2 is an A350V mutation. In some embodiments of the invention, the one or more of: enhancing the binding of apocalmodulin to the IQ domain of IQSEC2; reducing the production of ARF6-GTP; inhibiting the constitutive activation of guanine nucleotide exchange factor (GEF) IQSEC2; increasing the surface expression of AMPA receptors in the brain or the cell; and/or increasing basal synaptic transmission in the brain or the cell, are previously detected in a cell culture model or in an animal model.

In some embodiments of the invention, the cell culture model or the animal model are based on an A350V mutation in the IQ domain of IQSEC2. The animal model may be in some embodiments, a CRISPR murine model.

In some embodiments of the invention, there is provided a method of screening for a potential candidate for treating autism, epilepsy and/or intellectual disability in a subject in need comprising contacting a cell culture or an animal with the potential drug and detecting one or more of the following features:
  enhancing with the binding of apocalmodulin to the IQ domain of IQSEC2;
  reducing the production of ARF6-GTP;
  inhibiting the constitutive activation of guanine nucleotide exchange factor (GEF) IQSEC2;
  increasing the surface expression of AMPA receptors the brain or a cell; and/or
  increasing basal synaptic transmission in the brain or the cell,
wherein if the potential candidate is:
  enhancing the binding of apocalmodulin to the IQ domain of IQSEC2;
  reducing the production of ARF6-GTP;
  inhibiting the constitutive activation of guanine nucleotide exchange factor (GEF) IQSEC2;
  increasing the surface expression of AMPA receptors the brain or the cell; and/or
  increasing basal synaptic transmission in the brain or the cell,
then the potential drug is suitable for treating autism, epilepsy and/or intellectual disability in a subject.

In some embodiments of the invention, the increasing the surface expression of AMPA receptors the brain is in the hippocampal tissue.

In some embodiments of the invention, the AMPA receptors in the brain are GluA2 AMPA receptors.

In some embodiments of the invention, the autism, epilepsy or intellectual disability are associated with a mutation in the IQ domain of IQSEC2.

In some embodiments of the invention, the mutation in the IQ domain of IQSEC2 is an A350V mutation.

In some embodiments of the invention, the cell culture model or the animal model, which can be for example a CRISPR murine model are based on an A350V mutation in the IQ domain of IQSEC2.

In some embodiments of the invention, the cell culture model is derived from a subject having a mutation in the IQ domain of IQSEC2 and may be in some embodiments, an induced pluripotent stem cells (IPS).

In some embodiments of the invention, the autism is at least one of non-syndromic autism, classical autism, Asperger's syndrome, Rett's syndrome, childhood disintegrative disorder, or pervasive developmental disorder not otherwise specified (PDD-NOS).

Induced pluripotent stem cell technology allows one to create a human disease model from patients in which one can study basic cellular processes involved in the disease and use as a platform for drug therapy. The procedure involves (with Human Subjects approval) taking a small piece of skin and growing fibroblasts from this skin. The fibroblasts are then transfected with four genes that have been shown to return the fibroblasts to a pluripotent state (stem cell) from which they may be differentiated into any cell type depending on the growth conditions used to culture the stem cells. An important aspect of this approach to study human disease is that the stem cells themselves can be genetically modified to remove the disease-causing mutation (reverting the DNA sequence of relevance to the normal sequence) thereby allowing one by comparison of the parent cells and corrected cells to know what differences are actually due to the mutation. This helps one guide and select targets for drug therapy. In one embodiment of the invention, the stem cells so derived from the fibroblasts (and corrected using CRISPR technology) can then be differentiated into neurons using specific growth factors. This can be done using fibroblasts taken from the child with the A350V mutation (with institutional approval and parental consent) and have studied the biology of the neurons differentiated from the stem cells produced from this child as well as the corrected stem cells. Functional differences between the cells of the child and the corrected cells in their electrophysiological properties (decreased basal synaptic transmission) similar to what those described in the A350V mice. In addition, early on the development of these cells that shown to have an increased propensity to undergo repetitive depolarizations similar to what one would see in epilepsy making them a good source for studying epilepsy. An additional finding in these cells is that the neuronal cultures derived from these cells are deficient in the production of cells producing the neurotransmitter GABA-producing an inhibitory excitatory imbalance and possibly explaining the increased epilepsy inpatients with A350V. This would also suggest that GABA replacement therapy may be efficacious in preventing these seizures.

The stem cell derived neuronal cultures may therefore be used to study processes that mimic epilepsy, that mimic changes in the trafficking of membrane receptors that we see in vivo in the mice model and to serve as a platform for drug discovery. Another emerging use of the neurons derived from the stem cells is the development of organoid structures-in vitro developed cell cultures in which cells develop into a network of interconnecting neurons which communicate with one another and may actually mimic properties of brain tissue as opposed to isolated cells. These organoids also derived from A350V may be used for drug development as well.

Currently using the cell culture model AMPA receptor trafficking, production of GABAergic neurons and ARF6 activation are assessed as targets for drug therapy. Costs of working in vitro with the stem cells is much less than working in the mice and allows a more rapid throughput system for screening drugs. Thus, the invention further provides two types of IPSCs-those directly from the child with the A350V mutation and then the mutation is corrected to produce A350A (changing the V back to an A). This allows us to say that differences seen between the two IPSCs is due to differences in IQSEC2.

In some embodiments of the invention, there is provided a cell culture having an A350V mutation in the IQ domain of IQSEC2. In some embodiments of the invention, the cell culture is derived from a child having a mutation in A350V mutation in the IQ domain of IQSEC2. In some embodiments of the invention, the cell culture has one or more of the following features:
  inhibiting the interference with the binding of apocalmodulin to the IQ domain of IQSEC2;
  enhancing the production of ARF6-GTP;
  enhancing the constitutive activation of guanine nucleotide exchange factor (GEF) IQSEC2;
  reducing the surface expression of AMPA receptors in a cell; and/or
  reducing the basal synaptic transmission in the cell.

In some embodiments of the invention, the cell culture is an induced pluripotent stem cells (IPS) derived from the human with the A350V mutation. Furthermore, these IPS cells can be differentiated into hippocampal neurons and used as a platform for drugs like the mice.

In some embodiments of the invention, the cell culture is an induced pluripotent stem cells (IPS) that in which the A350V mutation is corrected to A350A.

In some embodiments of the invention, there is provided an animal model, which is CRISPR murine model having a mutation in the IQ domain of IQSEC2. In some embodiments of the invention, the mutation is A350V mutation in the IQ domain of IQSEC2. In some embodiments of the invention, the animal model has one or more of the following features:
  inhibiting the interference with the binding of apocalmodulin to the IQ domain of IQSEC2;
  enhancing the production of ARF6-GTP;
  enhancing the constitutive activation of guanine nucleotide exchange factor (GEF) IQSEC2;
  reducing the surface expression of AMPA receptors in the brain; and/or
  reducing the basal synaptic transmission in the brain.

In some embodiments of the invention, the examples show an assessment of a drug that is an AMPA receptor positive allosteric modulator in the animal model of the invention. A mouse model and IPS (stem cell model) of autism, intellectual disability and epilepsy based on a human mutation in the IQSEC2 gene (Alanine for Valine substitution at amino acid residue 350) was used in the experiment described in Example 6. The mice were created by CRISPR with this mutation recapitulate the phenotype seen in man with increased epilepsy, ID, and autistic like features. Further, induced pluripotent stem cells from the child with the mutation and neurons from these cells can be used. Both models are believed to be a platform for drug development for ID, autism and epilepsy. The mechanism by which the A350V mutation results in intellectual disability and autism appears to be related to a down regulation of AMPA receptors. These receptors have been implicated in learning and memory and social behavior. It was therefore proposed that increasing AMPA receptors in the brain will provide clinical benefit. The drug initially made by Pfizer (PF-04958242) and then purchased by Biogen (BIIB 104) is a first in class AMPA receptor positive allosteric modulator which is now in phase 2 clinical studies for treating intellectual disability. This drug is now under investigation to assess the ability of this drug to correct the deficiency in AMPA receptors in the A350V model and thereby provide clinical benefit (improve cognitive function and autistic features. Specifically, the ability of the drug to increase AMPAR expression in the brain and to improve the learning, memory and social behavioral defects seen in A350V mice is now assessed and it is believed that the drug will be beneficial in this animal model and hence is a good candidate for treating a patient having a mutation in the mutation in the IQ domain of IQSEC2 and in particular an A350V mutation.

In some embodiments of the invention, there is provided a method of using of the A350V platforms (mice and stem cells) for identifying drug for treating epilepsy as the A350V mutation results in a form of epilepsy that is resistant to all known treatments.

These A350V platforms (mice and stem cells) will be useful also for assessing and developing candidate drugs for treating epilepsy. The A350V mice have seizures and the IPSC derived neurons from the child with the mutation displays electrophysiological features consistent with epilepsy making this an ideal platform to check new drugs that can prevent epilepsy. Over 30% of all cases of epilepsy are drug resistant and this A350V model will provide a new venue and mechanism of action on which drugs may be assessed to prevent seizures.

The studies exemplified herein provide new findings for understanding the regulation of IQSEC2 activity and the pathophysiology of a new IQSEC2 mutant (A350V) with implications for drug therapy. First, it was demonstrated that calcium increases the binding of IQSEC2 to calmodulin and the data with previously reported conflicting results. Second, the first mutation identified in humans associated with a constitutive activation of Arf6 due to a constitutive increase in IQSEC2 GEF activity was reported Third, it was demonstrated that surface GluA2 AMPA receptors are decreased in the brains of A350V IQSEC2 mice. Finally, it was demonstrated that A350V IQSEC2 mice have abnormal behavioral phenotypes with increased locomotion, abnormal social interactions and decreased learning.

It was demonstrated in two different systems, in vitro with cell extracts and in cells, that apocalmodulin can bind to IQSEC2 and that this binding is impaired with the A350V mutant. In a resting cell (i.e., HEK 293T cells, neurons) the cytoplasmic concentration of free calcium is 50-100 nM (Persechini and Cronk et al, 1999) with localized calcium concentrations of 1-10 μM being achieved with an appropriate stimulus (i.e. N/MDA receptor activation in neurons). The $K_d$ of calcium for calmodulin is approximately 1 μM with essentially no calcium calmodulin being found in a cell with a free cytoplasmic calcium of less than 200 nM (Persechini and Cronk et al, 1999). The demonstration that half-maximal interaction between calmodulin and IQSEC2 occurs at around 1 μM calcium is therefore physiologically relevant.

However, while A350V binds less efficiently to apocalmodulin as compared to wild type IQSEC2, the A350V mutant is capable of binding calcium-calmodulin equivalent to or even superior to wild type IQSEC2. Similar to myosin (Trybus et al, 2007) the epitope or conformation within the IQ region of IQSEC2 recognized by apocalmodulin and calcium calmodulin may be different. The finding that A350V IQSEC2 can effectively bind to calcium-calmodulin but not apocalmodulin may suggest that the alpha helical distortion of the IQ domain in the A350V IQSEC2 mutant induced by the valine-for-alanine substitution introduces a change in the conformation of the IQ motif of IQSEC2 that is similar to the conformation of the IQ motif that is induced in wild type IQSEC2 by the binding of calcium calmodulin. The wild type IQSEC2 IQ motif may adopt a relaxed conformation in which apocalmodulin may bind when calcium-calmodulin is not present; however, in the A350V mutation the conformation of the IQ region may be locked in a conformation which will not allow it to assume a conformation permissive for apocalmodulin binding.

This is the first demonstration of a human disease resulting from a constitutive activation of Arf6 due to a constitutive increase in IQSEC2 GEF activity. It was shown that the IQSEC2 GEF activity for Arf6 is increased in cells expressing mutant A350V IQSEC2 as compared to wild type IQSEC2. Ionomycin treatment of cells expressing WT IQSEC2 induced a significant increase in Arf6 activation, indicating a calcium-dependent regulation of Arf-GEF activity. The A350V mutant, however, already had a high level of basal activity that was comparable to WT IQSEC2 after treatment with ionomycin. All previously reported mutants of IQSEC2, including R359C, which is also located in the IQ region, have been noted to have decreased Arf6 GEF activity (Shoubridge et al, 2010). It was also shown that the GEF activity of the R359C mutant is not elevated by ionomycin treatment, which suggests that deficits in calcium dependent regulation of this mutant may contribute to ID. It is proposed that the constitutive activation of IQSEC2 GEF activity by the A350V mutation may be due to the mutation locking the IQ motif into the same conformation as wild type IQSEC2 bound to calcium-calmodulin (wherein IQSEC2 GEF activity is increased).

A key factor underlying the strength of individual excitatory synapses is the number of AMPA receptors at synapses. Trafficking of AMPA receptors to and from synapses plays a key role in synaptic transmission and in experience-dependent synaptic plasticity and associative learning (Qin et al, 2005; Rumpel et al, 2005; McCormack et al, 2006; Hu et al, 2007; Matsu et al, 2008; Kielland et al, 2009; Zhu, 2009). NMDA receptor-induced removal of GluA1/2 AMPA receptors from synapses is a key step in the induction of long-term depression (LTD), and Arf6 activation is a necessary component of this type of plasticity (Brown et al, 2016; Scholz et al, 2010). IQSEC2 regulates AMPA receptor currents (Myers et al, 2012; Brown et al, 2016). The Arf-GEF activity of IQSEC2 is required for LTD, as ID-linked mutations in IQSEC2 that decrease its Arf-GEF activity impair its induction (Brown et al, 2016). This indicates that properly regulated activation of Arf6 by IQSEC2 is necessary for normal synaptic plasticity processes, including the regulated removal of AMPA receptors in LTD. The findings here showing that increased Arf6 activity is associated with decreased GluA2 AMPA surface expression in A350V mutant brain tissue is consistent with the critical role of Arf6 in regulating the removal of AMPA receptors from the plasma membrane (Brown et al, 2016). The demonstration that basal hippocampal synaptic transmission is decreased in A350V IQSEC2 mice is also consistent with a down-regulation of AMPA receptors in this model.

Based on the data presented here and previous work presented by others (Myers et al, 2012; Brown et al, 2016) FIG. 10 shows a model for the activation of wild type IQSEC2 by calcium as well as the pathophysiological consequences of the A350V IQSEC2 mutation. In the presence of wild type IQSEC2, the binding of glutamate to the NMDA receptor leads to calcium influx and a rise in free intracellular calcium. This calcium binds to calmodulin and the binding of calcium calmodulin to the IQ site on IQSEC2 induces the GEF activity of IQSEC2 allowing it to promote the formation of Arf6-GTP. Arf6-GTP, in turn, regulates endocytosis of surface AMPA receptors by pathways that are poorly understood, but which may include JNK (Myers et al, 2012). On the other hand, in the A350V IQSEC2 mutant, IQSEC2 GEF activity for Arf6 is constitutively activated resulting in persistently increased Arf6 activity, which may markedly downregulate surface AMPA receptors, specifically GluA2, (representing an exaggerated form of long-term depression). Thus, the normal processes for regulating AMPA receptor levels at synapses are compromised by the A350V IQSEC2 mutation. This hypothesis appears to provide a mechanistic basis for the defects in behavior and learning associated with the A350V IQSEC2 mutation. Furthermore, according to this hypothesis, treatment to restore the balance in AMPA transmission by blocking exaggerated AMPA downregulation may provide clinical benefit specifically an increase in learning potential. The size of the change in surface GluA2 AMPA induced by the A350V mutation is similar to what has been reported in mutations in the Thorase gene (Piard et al, 2018; Umanah et al 2017) where pharmacological attempts to restore normal surface AMPA activity have shown therapeutic benefit in man (Ahrens et al, 2017).

Behavioral phenotyping of the A350V IQSEC2 mice demonstrates increased locomotion, abnormal social interactions and learning impairments in the absence of motor coordination deficits. The increased preference for social novelty in the A350V mice described here, while different from what has been described in autism, has been described in other genetic encephalopathies with intellectual disability and abnormal social functioning such as Williams's syndrome (Martin et al, 2018; Ng et al, 2018). The behavioral findings in the A350V mice appear to model to some of the abnormal behaviors found in the human index case with the A350V mutation, specifically hyperactivity, abnormal social interactions with no inhibitions with strangers and impaired cognitive function. However, more complete behavioral phenotyping of the A350V IQSEC2 model will be required in order to properly define the spectrum of social interaction abnormalities, hyperactivity features, and the type of learning and memory impairment present in these mice. Decreases in surface AMPA receptors have been noted in other models of learning impairment (neurodevelopmental as well as Alzheimer's disease) and in models of social dysfunction (Ahrens et al, 2017; Piard et al, 2018; Umanah et al, 2017; Guntupalli et al, 2016; Tian et al, 2018; Kim et al, 2018) and increasing AMPA transmission has shown benefit in these models (Lauterborn et al 2016; Kim et al, 2018). Accordingly, strategies designed to restore surface AMPA in the A350V IQSEC2 mouse model may have a beneficial effect on cognitive and affective behavior and represents a potential actionable node for treatment in humans for the A350V IQSEC2 mutation.

EXAMPLES

Methods
DNA Constructs Used in this Study.

Figure 1A:
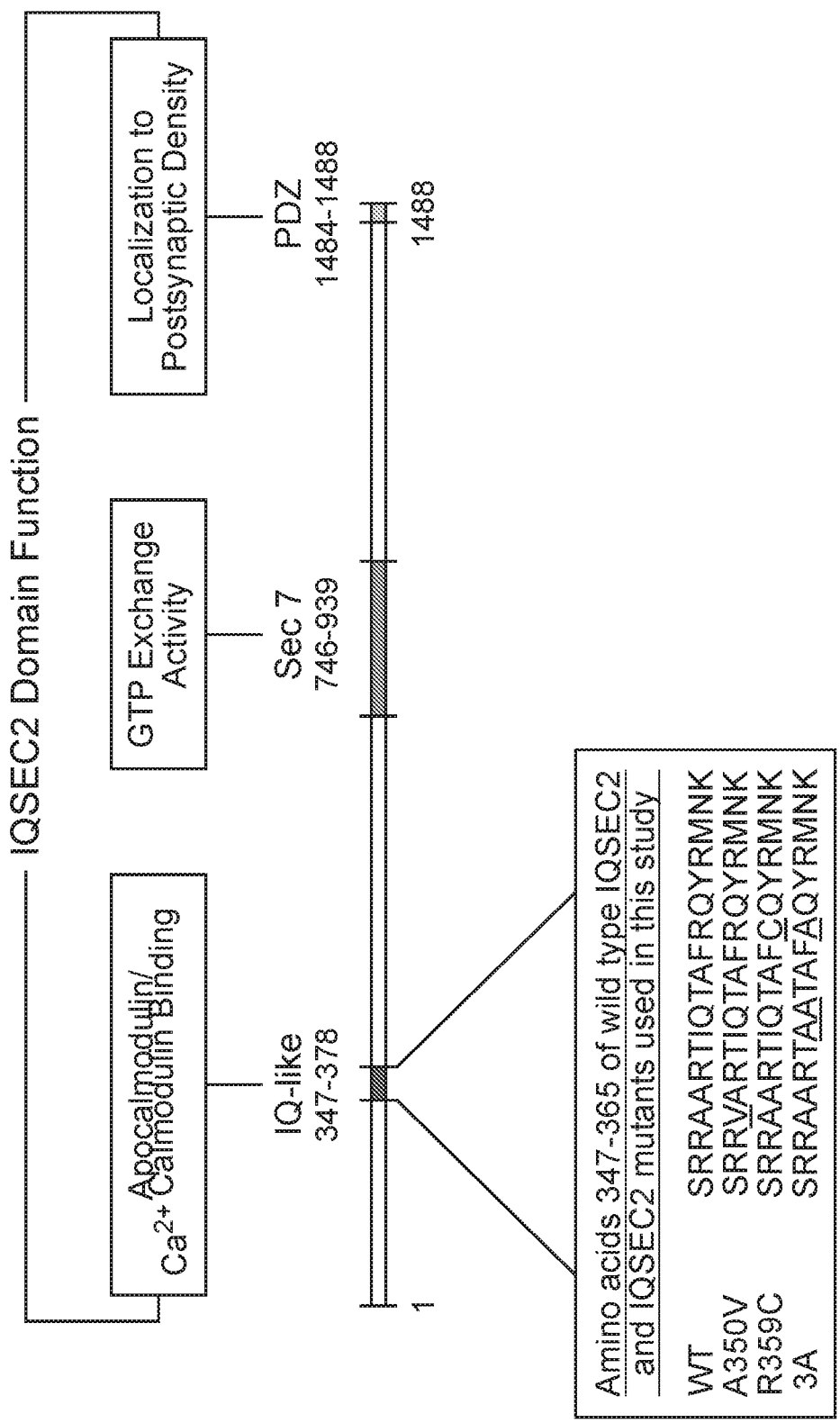
FIG. 1A shows IQ-like, IQ homology motif thought to be site for interaction of IQSEC2 with calmodulin (Shoubridge et al, 2010). SEC7, catalytic domain responsible for the GEF activity of IQSEC2 (Shoubridge et al, 2010). PDZ, domain reported to mediate interaction of IQSEC2 with the post-synaptic protein PSD-95 thereby localizing IQSEC2 to the postsynaptic density (Brown et al, 2016). Inset demonstrates the amino acid sequence within the IQSEC2 IQ domain of wild type IQSEC2 and sequence variants in this region, including A350V, used in this study. Underlined residues indicate site of sequence variance from the wild type.

The IQSEC2 wild type gene was cloned 3' to renilla luciferase and three copies of the HA tag in pcDNA3.1 Zeo (Genscript) or 3' to a FLAG tag in pCAGGS. The pcDNA3.1 construct expresses full length (1488aa) human IQSEC2 with an N-terminal renilla luciferase and HAx3 tag under the control of a CMV promoter, and also contains a zeocin (Zeo) gene allowing for selection of stable transformants expressing the IQSEC2 gene. Specific mutations were introduced into the renilla luciferase-wild type (WT) IQSEC2 vector or the FLAG wild type IQSEC2 vector for the studies described herein (GenScript) (FIG. 1a). For production of the A350V mutation the corresponding codon for IQSEC2 amino acid residue 350 was changed from GCT (Alanine) to GTT (Valine). Two additional mutant constructs were also generated in the IQ domain of IQSEC2: (1) a previously described IQSEC2 R359C mutation associated with ID (Shoubridge et al, 2010) and (2) a previously described engineered mutation containing three alanine substitutions in the IQ region at amino acid residues 354, 355 and 359 (herein called 3A) (Myers et al, 2012). All IQSEC2 constructs were verified by DNA sequencing. The genes for calmodulin (human Calm1 (NM_006888), Calm2 (NM_001743) and Calm3 (NM_005184) were obtained from a human ORFeome library (Yang et al, 2011) and subcloned into pcDNA3 to have a C-terminal triple FLAG tag.

Cell Culture and Stable Cell Lines Expressing IQSEC2

HEK293T cells were propagated in DMEM with low glucose and 10% fetal calf serum (FCS). Stable cell lines (expressing either wild type or mutant A350V IQSEC2) were produced in 293T cells using selection with Zeo (200 µg/ml) after transfection with calcium phosphate.

Arf6 Activation Assay

For the assessment of Arf6-GTP by ELISA, cell extracts were prepared from HEK293T cells stably expressing either wild type or A350V IQSEC2. ELISA was performed exactly according to manufacturer's protocol (G-LISA Arf6 activation assay, Cytoskeleton Inc). The amount of Arf6-GTP was assessed using immobilized GGA peptide. Normalization was by total protein and/or luciferase as described in results.

For the assessment of Arf6-GTP using a GGA-3 pulldown assay and western blot, HEK293T cells were transfected with FLAG-tagged WT, A350V, or R359C IQSEC2 in pCAGGS vector by calcium phosphate. Twenty-four hours after transfection, the cultures were treated with 5 µM ionomycin or ethanol vehicle for 5 mins, then lysed in 50 mM Tris-HCl, pH 7.5, 100 mM NaCl, 2 mM $MgCl_2$, 0.2% SDS, 0.5% sodium deoxycholate, 1% Triton X-100, 10% glycerol, and 1× Halt protease inhibitor cocktail. An Arf6-GTP pull-down assay was carried out as described (Shoubridge et al, 2010). Briefly, lysates were cleared by centrifugation at 10,000 rpm for 10 min and incubated with GGA3:GST on glutathione-sepharose beads for 5 hours at 4° C. The beads were washed and bound proteins were eluted and probed by immunoblot with rabbit anti-Arf6 (1:750, Cell Signaling #5740). Lysates were also probed against total Arf6 and with rabbit anti-FLAG (1:1000; Covance #PRB-132P) to detect expression of FLAG-IQSEC2. Bands were visualized with the use of a LiCor Odyssey imaging system and quantified with Image Studio Lite. Each band was normalized to the untreated sham-transfected control. The data were statistically analyzed by one-way ANOVA followed by Tukey's Multiple Comparison Test for post-hoc analysis.

Assessment of Binding of IQSEC2 to Calmodulin In Vitro.

The binding of wild type and mutant IQSEC2 to calmodulin was assessed in vitro using calmodulin-sepharose (BioVision, Milipetas, CA). Extracts from stably transfected cells were prepared in either buffer A [50 mM Tris pH 7.5; 150 mM NaCl, 10 mg/ml BSA; 5 mM EGTA and 0.1% Triton X-100] or buffer B [10 mM Tris pH 7.5; 150 mM NaCl, 5 mM EGTA, 5% glycerol, 0.5% Triton X-100]. Extracts were clarified by centrifugation at 14000 rpm at 4° C. to remove insoluble debris and the amount of luciferase activity in the extract assessed using the Promega luciferase assay system and a Turner TD 20/20 luminometer. Extracts (10,000-100,000 luciferase units) were then incubated in buffer A or buffer B with or without $CaCl_2$ in a total volume of 1 cc. The concentration of free calcium in the incubation conditions was calculated using the maxchelator algorithm (maxchelator.stanford.edu) which is based on the ionic strength, pH, temperature and dissociation constant of EGTA for calcium. The concentration of free calcium used in these studies ranged from 0.73 nM to 2 mM. 10 µl of calmodulin-sepharose was added to the incubation and mixed on a rotary apparatus for 3-4 hours. The calmodulin-sepharose was washed twice with binding buffer, resuspended in 100 µl of luciferase reagent lysis buffer and 20 µl was assessed for luciferase activity.

Assessment of Binding of IQSEC2 to Calmodulin in Cells.

Assessment of an interaction between wild type and mutant renilla luciferase IQSEC2 constructs (wild type or mutants) and 3×FLAG tagged candidate interactors (calmodulin proteins Calm1 (NM_006888), Calm2 (NM_001743), and Calm3 (NM_005184) in HEK293T cells was performed using the Lumier assay (Taipale et al, 2012), with an automated robotic system. Briefly, constructs were cotransfected using polyethylenimine (PEI), in 96 well plates. Cells were lysed at 48 h in lysis/wash buffer [50 mM Hepes pH 7.9; 150 mM NaCl; 2 mM EDTA; 0.5% Triton X-100, 5% glycerol] and candidate interactors were pulled down in anti-FLAG antibody (Sigma, F1804) coated 384 well plates for 3 hours at 4° C. The amount of renilla luciferase activity in anti-FLAG captured protein was used as a readout of the strength of the interaction between renilla-IQSEC2 and interactor-FLAG. Interaction scores designate renilla activity after pulldown normalized to FLAG ELISA, to account for potential variability in interactor levels. GFP-FLAG was used as a negative control interactor and its interaction strength and score were considered background levels. Each experiment was performed with 2-4 replicate wells for each pair of IQSEC2 (wild type or mutant) and each calmodulin. In addition, independent replicate experiments were performed on different days, four repeat experiments for the wild type IQSEC2 and the A350V mutant and two repeat experiments for the R359C and 3A mutants. Renilla activity was also measured in whole cell lysates (negative control cells, cotransfected with GFP-FLAG) in order to verify that the observed differences in interaction scores between wild type and mutant IQSEC2 and the calmodulins were not due to differences in cell viability or transfection efficiency.

Generation of A350V IQSEC2 Mice by CRISPR.

Mice were generated by CRISPR at Applied Stem Cells (Milipitas, CA). Murine IQSEC2 (NM_001005475.2) was targeted with the goal of generating an A350V mutation identical to that found in the human index case in which the codon GCT (Ala) at amino acid 350 is mutated to GTT (Val) with an additional AGG to CGT silent mutation (R349) in order to prevent the guide RNA g20 GGCAGCCCTGCGGCTCAGGA (SEQ ID No. 1) from targeting the same allele after repair. A single stranded oligonucleotide donor (ssODN) was synthesized with two homology arms flanking the GCT to GTT mutation site [5'CTGAGCTGCGCAGCCGCTCAAAGTTCTTATTCATACGGTACTGTCGAAAGGCT GTCTGGATGGTCCTGGCAACACGGCGGCTCAGGAAGGAGCCCCCATACTTCCTCT CCAGCATTTCCACCTGTCAGAGGAACAAGTTCAGAAAG3'] (SEQ ID No. 2) serving as the repair template during the process of homology directed repair (HDR). Synthesized ssODN donor, g20 gRNA transcripts and Cas9 mRNA were microinjected into the cytoplasm of C57BL/6J embryos. Identification of F0 successfully targeted mice were identified by Sanger sequencing. Germline transmitted F1s containing the mutation were used to generate the A350V colony used for all additional studies and continued breeding of the mice was done in a C57Bl/6J background. Approximately 1 kb of DNA was sequenced on both sides of the mutation with no other changes detected. Wild type (WT) and A350V IQSEC2 protein were also assessed by western blot from mouse brains and they were found to be of the same size as predicted. MRI structural analysis of both wild type and A350V mice revealed no gross differences in brain volume or gross structural differences in A350V mice. Hemizygous males, heterozygous and homozygous females were fertile and were housed in a germ-free animal facility and used for breeding and the studies described.

All studies for which the mice were used were approved by the Institutional Animal Care and Use Committee of the Technion Faculty of Medicine (protocols IL0360212 and IL1691117).

Flow Cytometry Analysis for Surface AMPA Receptors of Hippocampal Neurons from Wild Type and A350V IQSEC2 Mutant Mice A single cell suspension from the mouse hippocampus was prepared by mechanical dissociation using the gentleMACS dissociator (Miltenyi Biotec, Gladbach, Germany) coupled with tissue enzymatic degradation using the Adult Brain Dissociation Kit (Miltenyi Biotec). The cell suspension was mesh-filtered (70 micron) to remove clumps and debris and red blood cells were removed by a Red Blood Cell Removal Solution (Miltenyi Biotec). A highly enriched population of neurons were obtained from this cell suspension by depleting non-neuronal cells using the Neuron Isolation Kit (Miltenyi Biotec). Non-neuronal cells are removed in this method using biotin-conjugated monoclonal antibodies specific for non-neuronal cells followed by anti-biotin monoclonal antibodies coupled to magnetic microbeads.

For flow cytometric analysis of membrane bound GluA1/2 Alex Fluor 647 fluorochrome-conjugated to Anti-GluA1/2 antibody (Santa Cruz, sc-517265) was used. This antibody recognizes an epitope present in both GluA1 and GluA2. Neurons were incubated with the antibody for 30 minutes at 4° C. and were then washed with a phosphate-buffered staining solution (Dulbecco's phosphate buffered saline with calcium, magnesium, glucose, pyruvate and 0.5% bovine serum albumin). Samples were analyzed on a LSRFortessa cell analyzer using FlowJo software.

Surface Protein Cross-Linking Assay to Detect Surface AMPA Receptors in Hippocampal Tissue from Wild Type and A350V IQSEC2 Mice To determine the relative distribution of surface AMPA receptors in the hippocampus of IQSEC2 A350V as compared to wild type IQSEC2 a surface protein-crosslinking assay was performed using membrane-impermeant cross-linking agent, Bis(sulphosuccinimidyl)suberate ($BS_3$, Sigma) as previously described (Umanah et al, 2017) with some modifications. Bis(sulphosuccin-imidyl)suberate ($BS_3$) is a membrane-impermeant crosslinking agent that selectively crosslinks cell-surface proteins, forming high-molecular-mass aggregates. Non-crosslinked intracellular proteins still retain their normal molecular mass. Brains from wild type or IQSEC2 A350V mice littermates were rapidly removed and the hippocampi were dissected on ice and stored at −80° C. until further processing. The frozen tissue was cut into small pieces. Each sample was divided into two and transferred to 1.5 ml Eppendorf tubes containing ice-cold PBS buffer with or without 2 mM $BS_3$ followed by 3 hours incubation at 4° C. with gentle agitation. Tissues were quenched with 0.1 M glycine in PBS (10 min, 4° C.) and lysed in ice-cold lysis buffer (PBS with 1% Triton-X100, 0.5% SDS, 5 mM ETDA, pH 7.4, and protease inhibitor cocktail). The lysates were homogenized and centrifuged at 15,000 g for 5 min. The total protein concentrations in the supernatants were determined. 20 ug of total protein from each sample was resolved on 10% SDS-PAGE and western immunoblotting was performed to analyze the surface and intracellular pools of AMPA receptors using anti-GluA1 (rabbit monoclonal, Abcam, Ab109450) (1:1,000), anti-GluA2 (rabbit monoclonal, Abcam Ab150387) (1:2,000), anti-GluA3 (rabbit monoclonal, Abcam Ab40845) (1:1,000), anti-GluA4 (goat polyclonal, Abcam Ab115322) (1:1,000), HRP conjugated polyclonal goat anti-rabbit (Cell signaling 7074), HRP conjugated polyclonal rabbit anti-goat (Invitrogen 611620) and HRP conjugated monoclonal mouse anti-beta-actin (Millipore-SIGMA, A3854) (1:5,000). The signal on blots were generated with VisiGlo™ HRP Chemiluminescent Substrate Kits (1B1583, AMRESCO) and imaged captured by Amersham Imager 600. The band intensities of all blots were measured using NIH ImageJ software (Rasband, W.S., NIH). All experiments were performed with five biological replicates and quantitative data are presented as the mean±standard error of the mean (SEM) performed by GraphPad prism6 software (Instat, GraphPad Software). Statistical significance was assessed by t-test (two-tailed). Assessments were considered significant with a p<0.05.

Immunocytochemistry of Hippocampus for Surface AMPA Receptor GluA2 from Wild Type and A350V Mice Mice were anesthetized and transcardially perfused with 4% paraformaldehyde (PFA) in PBS after a brief vascular system washing with PBS as previously described (Umanah et al, 2017). After perfusion, brains were removed and postfixed overnight with 4% PFA plus 4% sucrose in PBS. Brains were paraffinized and sectioned. Brain sections were then deparaffinized and blocked with 5% normal goat serum for 1 hour at room temperature (RT). To label surface GluA2, sections were incubated at 4° C. overnight in PBS containing mouse monoclonal anti-N-terminal GluA2 Alexa 488-conjugated antibody (Millipore-SIGMA, MAB397A4). After four washes with PBS, sections were incubated with permeabilization buffer with 0.3% Triton X-100, 2.5% normal goat serum in PBS, and rabbit monoclonal anti-C-terminal GluA2 antibody (Abcam, Ab150387) to label total GluA2 for 4 hours. The sections were then incubated in PBS containing goat anti-rabbit IgG Alexa Flour Plus 555 conjugated secondary antibody (ThermoFisher Scientific, A32732) for 1 hour at RT after four washes with PBS. Sections were then stained with DAPI for 5 minutes. After four washes with PBS, sections were mounted on precleaned slides with Immuno-Mount (Thermo Scientific). Images were acquired using a Zeiss LSM laser-scanning confocal microscope. Images for all conditions in individual experiments were analyzed by using identical acquisition parameters and were thresholded using identical values. The fluorescence intensities of labeled surface and internalized receptors were measured using ZEN software (Zeiss). Total and surface expression were normalized to the DAPI signal. Data are presented as mean SEM. The average fluorescence intensity of group results was used to determine the statistical significance by t-test (two-tailed) with a p<0.05 being considered statistically significant.

Electrophysiological Studies
Animals and Housing Conditions

Electrophysiological testing was performed on A350V IQSEC2 and wild-type (WT) IQSEC2 males on the same genetic background (C57BL/6J) at 18-20 weeks of age. Animals were housed 1-5 per cage in a 12 h light-dark cycle with food and water ad libitum. Experiments were conducted during the light phase.

Slice Preparation

Animals were anaesthetized by isoflurane inhalation and decapitated. Coronal brain slices (360-400 µm thick) were cut using a vibrating slicer (Leica VT1200, Nussloch, Germany). Slices were prepared in a choline-based solution containing 110 mM choline chloride, 2.5 mM KCl, 1.25 mM $NaH_2PO_4$, 0.5 mM $CaCl_2$, 7 mM $MgSO_4$, 26 mM $NaHCO_3$, 11 mM glucose, 11.6 mM sodium ascorbate, and 3.1 mM sodium pyruvate. Slices were cut in the midline to produce two individual slices from each section. The slices were incubated for 30 min in a sucrose-based solution containing 78 mM NaCl, 68 mM sucrose, 26 mM $NaHCO_3$, 2.5 mM KCl, 1.25 mM $NaH_2PO_4$, 2 mM $CaCl_2$, 2 mM $MgCl_2$, and 25 mM glucose. Slices were then allowed to recover for at least 60 min in artificial cerebrospinal fluid (ACSF) containing 119 mM NaCl, 2.5 mM KCl, 4 mM $CaCl_2$, 4 mM $MgCl_2$, 1 mM $NaH_2PO_4$, 26 mM $NaHCO_3$, and 11 mM glucose, at pH 7.4 and 290 mOsm. All solutions were saturated with carbogen (95% $O_2$ and 5% $CO_2$) at room temperature.

Input/Output Curve

Field potential evoked responses were recorded from the dendritic region of CA1 pyramidal neurons, with bipolar stimulation at the Schaffer collateral fibers, using Multi-clamp 700A amplifier (Axon instruments). All recordings were made in circulating ACSF saturated with carbogen at 30° C. After stabilization of the response, an input/output (I/O) curve was generated Behavioral Tests
Animals and Housing Conditions Behavioral testing was performed on A350V IQSEC2 and wild type (WT) IQSEC2 male and female mice on the same genetic background (C57BL/6J) at 5-7 weeks of age. Animals were housed in groups of 2-5 per cage in a reversed 12 hour light-dark cycle (dim light at 9:30 am, lights off at 10:00 am) with food and water available ad libitum. The housing room was maintained at 23±2° C. Experiments were conducted during the dark phase, under red lighting conditions (<5 lux), between 10 am and 7 pm. All behavioral testing experiments were performed by the same two individuals who were blinded to the genotype of the animals. Any single animal was only handled by a single individual throughout these studies. Animals were handled for two consecutive days prior to the testing day except for the three-chamber sociability and social novelty tests (see below for details). On the testing day, mice were transferred to the testing room and were acclimated for an hour before the experiment commenced. All animal experiments were conducted in accordance with the United States Public Health Service's Policy on Humane Care and Use of Laboratory Animals and approved by the Institutional Animal Care and Use Committee of Technion—Israel Institute of Technology (IL1691117).

Behavioral Analysis

For all the experiments, the arena or apparatus was cleaned after each trial with 70% ethanol and then with double-distilled water. All experiments were video-recorded by a camera (GUPPY PRO F-125B CCD) located above the arena and analyzed using Ethovision XT software version 10.1 (Noldus, Wageningen, The Netherlands), except for the Rotarod test which was recorded and analyzed using MAT-LAB R2017a (The Mathworks, Natick, MA, USA).

Open Field Test 5-6-week-old mice were placed in the center of a squared box arena (40×40×35 cm) made of white Derlin plastic and explored the novel environment for 5 minutes (Prut and Belzung, 2003). Velocity and distance were measured to assess locomotor activity. Anxiety-like behavior was measured by calculating the time spent in the center as compared to the perimeter of the arena. The arena was divided into 25 equal squared tiles with the center of the arena defined as the nine central tiles (40% of the arena) with each corner defined as a single tile.

Rotarod

Assessment of motor coordination was done using the Rotarod test (Med Associates Inc., Georgia, VT, USA) (Karl et al, 2003). 5-6-week-old mice were placed on a 32 mm diameter rod accelerating from 4 to 40 revolutions per minute (rpm) and latency to fall and end speed were measured. The test was performed on two consecutive days, each day consisting of four trials which lasted up to six minutes with an inter-stimulus interval of 10 min during which mice were placed in their home-cage.

Three-Chamber Sociability and Social Novelty Tests

Social interaction was measured in order to assess autistic-like behavior using a three-chamber test (Moy et al, 2004). Subject mice were assessed for the tendency to prefer an unfamiliar conspecific mouse (social stimulus; Stranger 1) over a novel object and over another unfamiliar mouse (novel social stimulus; Stranger 2). The arena (70×29×35 cm) was comprised of three chambers (side chambers 26×29×35 cm). 6-7-week-old mice (subject and stimulus) were habituated to the testing room for one hour on three consecutive days prior to the test day. Stimulus mice were further habituated to the wire cages (10.8 cm in height and 10.2 cm diameter; Galaxy Cup, Spectrum Diversified Designs, Inc., Streetsboro, OH, USA) for 20 minutes each day. On the test day, subject mice were habituated to the apparatus for 10 min and were allowed to explore all three empty chambers. Time spent in each chamber was measured to assess chamber bias. Following habituation, subject mice were assessed for social preference for 10 minutes by allowing interaction with Stranger 1 placed inside a wire cage in one chamber and a novel object placed inside an identical wire cage in the opposite chamber. Stimulus mice location was counterbalanced across trials to prevent chamber bias. Next, the novel object was replaced with Stranger 2 and social novelty was assessed for 10 minutes during which the subject mouse was able to choose between a novel mouse and an already familiar mouse. Time spent in each camber and in close interaction were measured for both the preference and novelty experiments. Stimulus mice were conspecific C57BL/6J mice from different litters, and were age, sex and weight-matched to the subject mice and to each other.

Morris Water Maze

The Morris water maze test was used to assess spatial learning and memory (Vorhees and Williams, 2006). 6-7-week-old mice were placed in a 120 cm circular diameter pool filled with water and a 15 cm diameter transparent platform that was placed at the Southwest (SW) quadrant, submerged 1 cm below the water surface. Water was maintained at 22.0±1° C. and made opaque by adding a dried milk powder. Mice were trained for four consecutive days, each day consisted of four trials with an inter-stimulus interval of 15 minutes during which mice were placed in their home-cage. During training, mice were released from a different quadrant in each trial and were given 60 seconds to find the platform. If the mice did not find the platform within 60 seconds, the experimenter guided the animal to the platform. After reaching the platform, mice were left on the platform for 10 seconds. On the fifth day a probe trial was performed in which the platform was removed from the maze, mice were released at the Northeast quadrant and given 60 seconds to explore the maze. Time spent in the SW quadrant served as an index of long-term memory.

Statistical Analysis of Behavioral Tests

All data were analyzed using MATLAB R2017a (The Mathworks, Natick, MA, USA). Summary statistics are presented as means±SEM. Lilliefors test was used to determine normality. Two-tailed Student's t-tests were used on normally distributed data. Mann-Whitney U-test was used to analyze data when sample size was not sufficient to establish normality.

Example 1

Figure 1B:
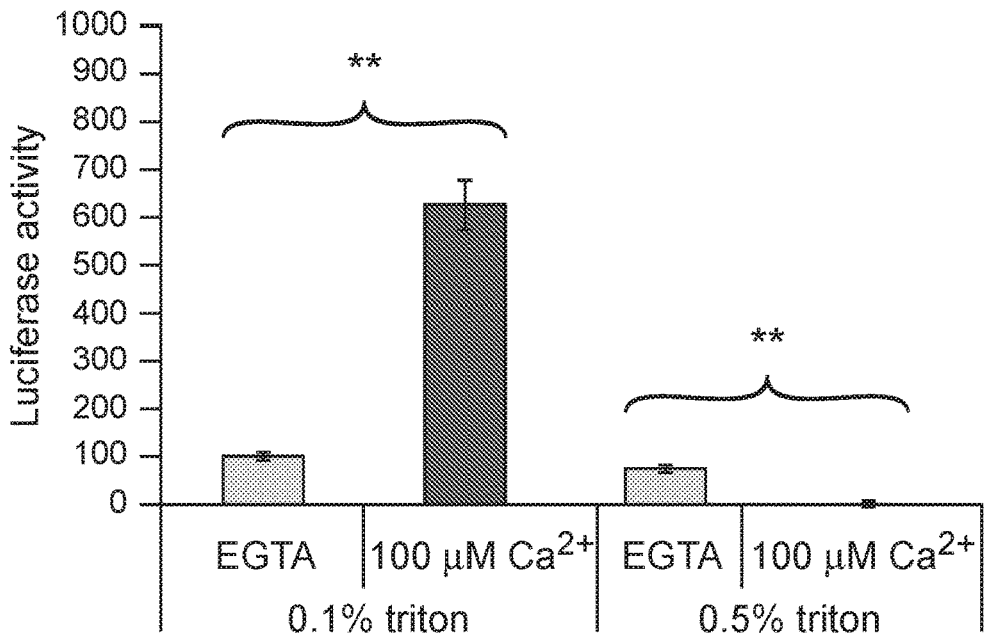
FIG. 1B shows the effect of calcium on the binding of IQSEC2 to calmodulin depends on the triton concentration in the cell extracts. Luciferase activity of the CM sepharose beads was used as a readout of the calmodulin IQSEC2-luciferase interaction. 293T cell extracts containing wild type IQSEC2 were prepared in low (0.1%) or high (0.5%) triton and used for binding studies with calmodulin sepharose as described in methods. In the presence of low triton concentration in the extracts, calcium resulted in a significant increase in the interaction between calmodulin and IQSEC2 (indicated by *, unpaired t-test, $p<0.001$, $n=6$)), while in the presence of high tritron calcium resulted in a significant decrease in the interaction between calmodulin and IQSEC2 (indicated by **, unpaired t-test, $p<0.001$, $n=6$).
Figure 1C:
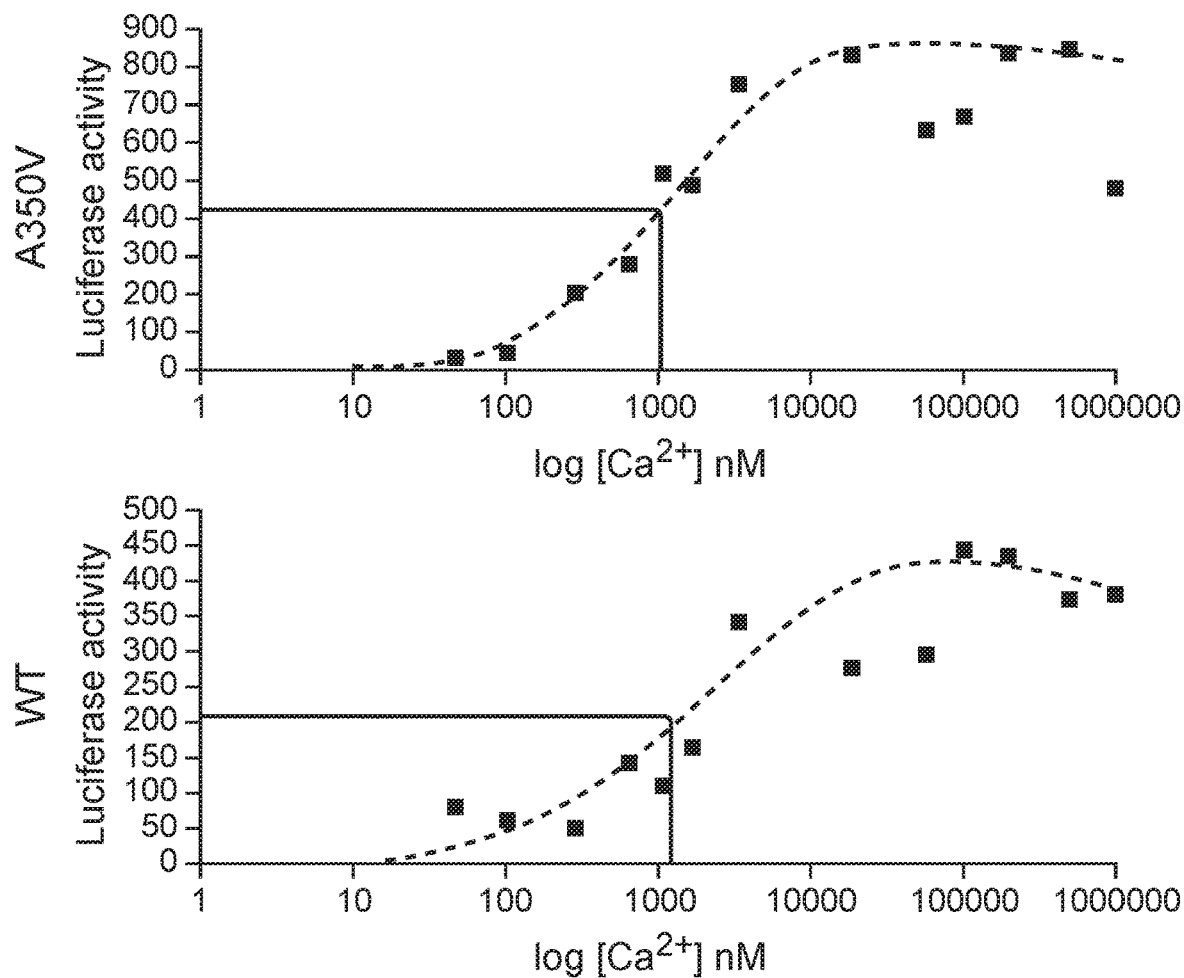
FIG. 1C shows that the binding of calmodulin to wild type and A350V IQSEC2 is increased by calcium. Cell extracts containing wild type or A350V IQSEC2 and binding studies between IQSEC2 and calmodulin sepharose under defined calcium concentrations were performed as described in methods. As shown for a representative experiment for both wild type and A350V IQSEC2, calcium resulted in an increase in binding of calmodulin to IQSEC2 with a similar calcium dose-response relationship (half-maximal binding (indicated by green line) of calcium-calmodulin for IQSEC2 at a free calcium concentration of approximately 1 µM for both wild type and A350V IQSEC2). The binding of calcium calmodulin was significantly increased for A350V IQSEC2 as compared to wild type IQSEC2 at all calcium concentrations greater than 200 nM (A350V 594±59.6 vs. wild type 271±41 luciferase units, $n=11$, unpaired t-test, $p<0.0005$).

In a Cell-Free System In Vitro Wild Type IQSEC2 Binds Significantly Better to Apocalmodulin as Compared to A350V and Calcium Increases Binding of Both Wild Type and Mutant IQSEC2 to Calmodulin As the A350V IQSEC2 mutation is in the IQ domain of IQSEC2 (FIG. 1a) and the IQ domains of many proteins have been demonstrated to bind to calmodulin (Bahler and Rhoads, 2002) it was first sought to determine how the A350V mutation would affect calmodulin binding to IQSEC2. Investigation of this interaction in a cell-free system in vitro using luciferase tagged IQSEC2 and calmodulin coupled to sepharose allowed for the precise control of calcium concentration which is known to dramatically affect the conformation and interactions of calmodulin with other proteins. In this system luciferase activity associated with calmodulin sepharose was used a quantitative readout of the calmodulin-IQSEC2 interaction. The IQ motif is present in over 100 proteins and in some cases preferentially binds to calcium-calmodulin while in other cases it binds preferentially to calcium-free calmodulin (apocalmodulin) (Bahler and Rhoads, 2002). Prior work on the IQSEC2-calmodulin interaction using myc-tagged wild type IQSEC2 and calmodulin sepharose [Myers et al, 2012] reported that apocalmodulin bound to IQSEC2 and that the addition of 2 mM calcium (thereby generating calcium-calmodulin) dramatically decreased the binding of calmodulin to IQSEC2. However, when the effect of calcium on the IQSEC2 calmodulin interaction was assessed, it was observed that calcium increased the binding of calmodulin to IQSEC2. Upon reviewing the buffers used by the research group in assessing binding of IQSEC2 to calmodulin, it was discovered that the concentration of Triton X-100 used in the binding and wash buffers was differed. As shown in FIG. 1b, at 0.1% Triton X-100, 100 uM calcium was associated with a several fold increase in binding of calmodulin to wild type IQSEC2 while at 0.5% Triton X-100, 100 μM calcium was associated with a several fold decrease in binding of calmodulin to wild type IQSEC2. Triton X-100 binds to most proteins via both hydrophobic and polar interactions [Singh and Kishore, 2006] and may thereby disrupt protein-protein interactions at high concentrations. An example of a calmodulin-interacting protein that is important for the calmodulin-IQ interaction is PEP-19 which binds to the C-terminal domain of calmodulin and electrostatically steers it to interact with the IQ domain [Wang and Putkey, 2016]. These results were interpreted as indicating that normally calcium stimulates calmodulin binding to IQSEC2 and that the results of Myers showing calcium reduces the binding of calmodulin to IQSEC2 were artifacts related to the high Triton concentration used. Therefore, for the in vitro studies comparing the interaction between calmodulin and wild type IQSEC2 as compared to mutant IQSEC2 low (0.1%) Triton X-100 was used. In the absence of added calcium (5 mM EGTA) it was observed that apocalmodulin bound significantly better to wild type IQSEC2 than A350V IQSEC2 (146±18 vs 48±8 luciferase units for wild type IQSEC2 as compared to A350V IQSEC2; n=6 experiments, unpaired t-test, p<0.001). The binding of wild type or A350V luciferase-IQSEC2 to calmodulin was assessed over a wide range of calcium concentrations. The Kd of calcium for calmodulin is 1 µM and it has been demonstrated that at free calcium concentrations of less than 200 nM all calmodulin exists as apocalmodulin and there is no calcium-calmodulin (Persechini and Cronk et al, 1999). As shown for a representative experiment in FIG. 1c for both wild type and A350V IQSEC2, calcium resulted in an increase in the binding of calmodulin to IQSEC2 with a similar calcium dose-response relationship (half-maximal binding of calcium-calmodulin for IQSEC2 at a free calcium concentration of approximately 1 µM for both wild type and A350V IQSEC2). The binding of calcium calmodulin was significantly increased for A350V IQSEC2 as compared to wild type IQSEC2 at all calcium concentrations greater than 200 nM (A350V 594±59.6 vs. wild type 271+/−41 luciferase units, n=11, unpaired t-test, p<0.0005). These data demonstrate that while A350V binds less efficiently than wild type IQSEC2 to apocalmodulin, the A350V mutant is capable of binding calcium-calmodulin equivalent to or even superior to wild type IQSEC2. As has been demonstrated for the binding of apocalmodulin and calcium calmodulin to myosin (Trybus, 2007) these data would suggest that the epitopes or conformations within IQSEC2 recognized by apocalmodulin and calcium-calmodulin are different.

Example 2

In Cells Wild Type IQSEC2 Binds More Effectively to Apocalmodulin than A350V IQSEC2

Figure 2A:
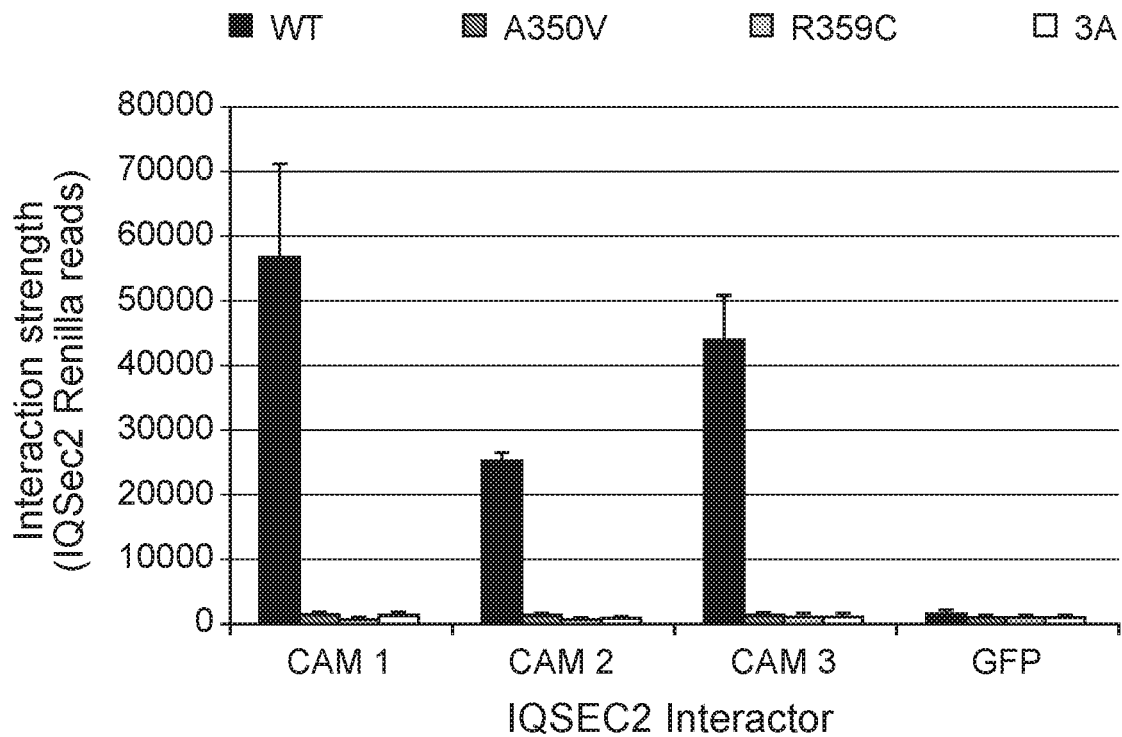
FIG. 2A shows the Interaction strength of wild type and mutant IQSEC2 proteins and calmodulins, measured as renilla luciferase-IQSEC2 activity after pulldown of calmodulin-FLAG proteins. Shown are mean and SD of 4 biological replicate wells for each pair of IQSEC2 calmodulin interactions.
Figure 2B:
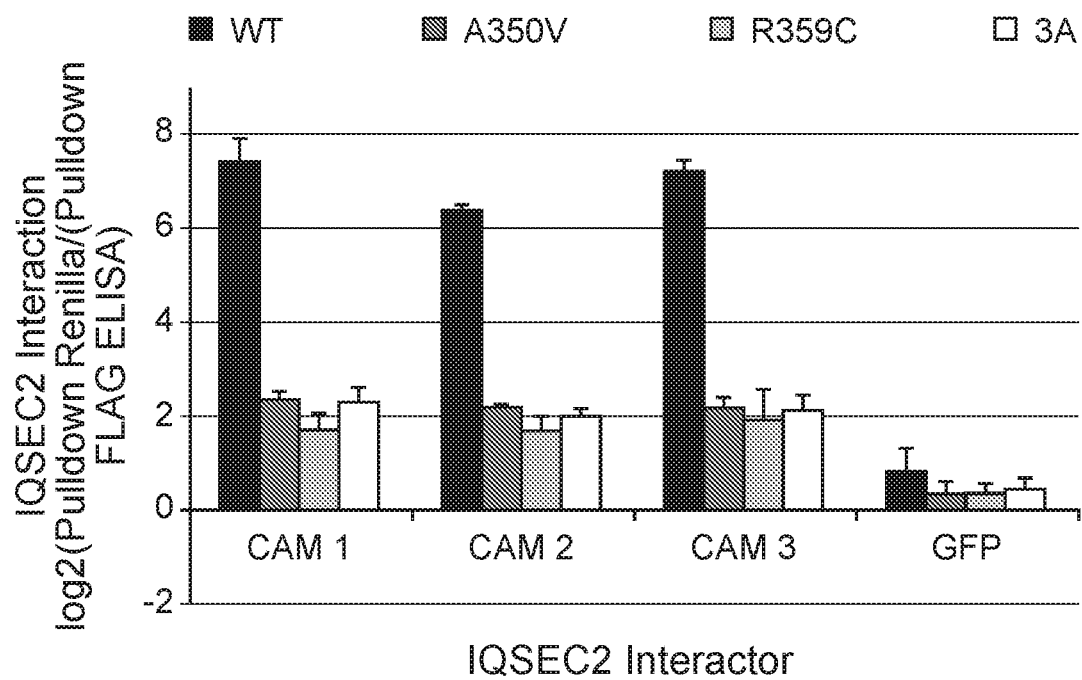
FIG. 2B shows the interaction score of wild type and mutant IQSEC2 proteins and calmodulins, measured as log 2 of renilla luciferase-IQSEC2 activity after FLAG pulldown divided by pulldown FLAG ELISA, to normalize for the interactor levels. Shown are the mean and SD of 4 biological replicate wells for each pair of IQSEC2 calmodulin interactions. Data comparing A350V IQSEC2 and wild type IQSEC2 are representative of four independent experiments done on independent days and the data for the R359C and 3a mutants are representative of two independent experiments done on independent days.

Nest it was sought to determine if differences in the binding of apocalmodulin to wild type and A350V IQSEC2 in cells similar to what was found in a cell free system can be demonstrated. In order to achieve this goal the binding of wild type and three mutant IQSEC2 renilla luciferase constructs (A350V, R359C, 3A) to three isoforms of human calmodulin in HEK293T cells using the Lumier assay as described in methods was assessed. In HEK cells, the intracellular calcium concentration is 50-100 nM so that all calmodulin is present as apocalmodulin (Persechini and Cronk, 1999). Significantly stronger binding of wild type IQSEC2 to all three apocalmodulin proteins as compared to the three mutant IQSEC2 constructs was observed. 34, 15, and 36-fold differences were observed between wild type and A350V IQSEC2 mutant with Calm1, Calm2 and Calm3 respectively (FIG. 2A) with similar fold changes seen for IQSEC2 mutants R359C and 3A. Importantly, the interaction strength of the mutants with the apocalmodulins was very close to background interaction levels, as measured for interactions with GFP (FIG. 2A) and GFP interaction was no different with wild type vs. mutant IQSEC2 (fold change of 1.07). Normalized interaction scores that take into account differences in the levels of the different interactors demonstrated 31, 14 and 31 fold higher interaction of wild type IQSEC2 with Calm1, Calm2 and Calm3 respectively compared to A350V IQSEC2 (FIG. 2B shown in log 2 scale). It was verified that the observed differences were not due to differences in cell viability or transfection efficiency as assessed by input luciferase activity of whole cell lysates. These data in cells are consistent with what was observed in a cell-free system, specifically that wild type IQSEC2 binds to apocalmodulin more effectively than A350V IQSEC2.

Example 3

Arf6 Activation is Increased in A350V IQSEC2 Stable or Transiently Transfected Cells as Compared to Wild Type IQSEC2

Figure 3A:
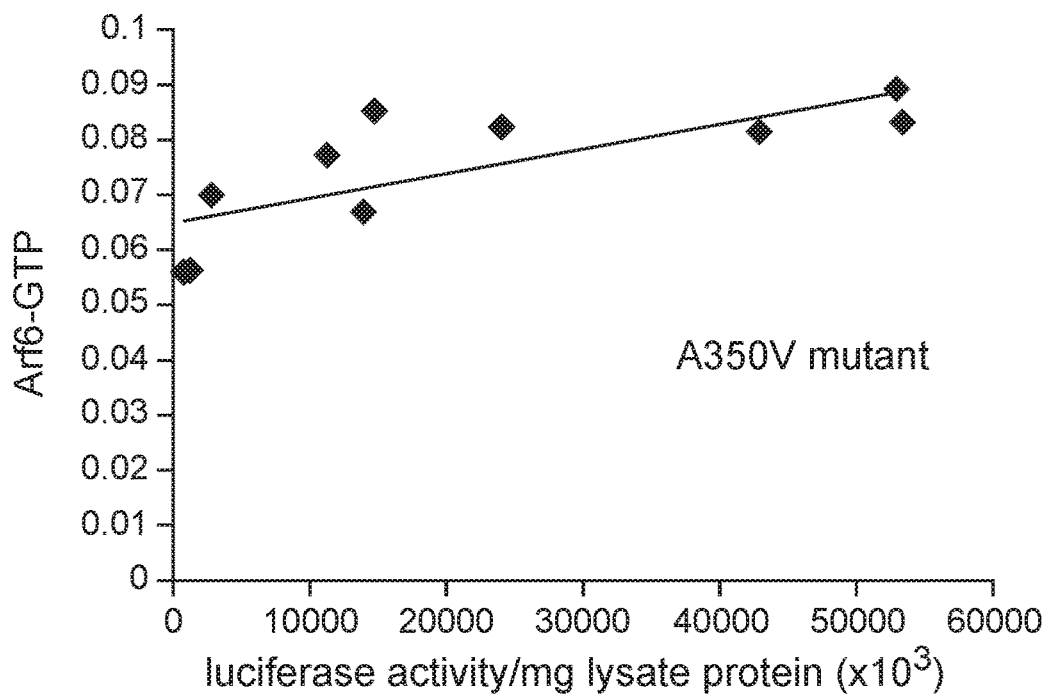
FIG. 3 A-B show the correlation between Arf6-GTP and luciferase in cell lines producing A350V (FIG. 3A) or wild type (FIG. 3B) IQSEC2 luciferase. Arf6-GTP was measured by ELISA (spectrophotometric units). The correlation between the relative amount of IQSEC2 and Arf6-GTP was significant for A350V (r=0.77, n=10, p=0.009) but not for WT IQSEC2 (r=0.52, n=6, p=0.28).
Figure 3B:
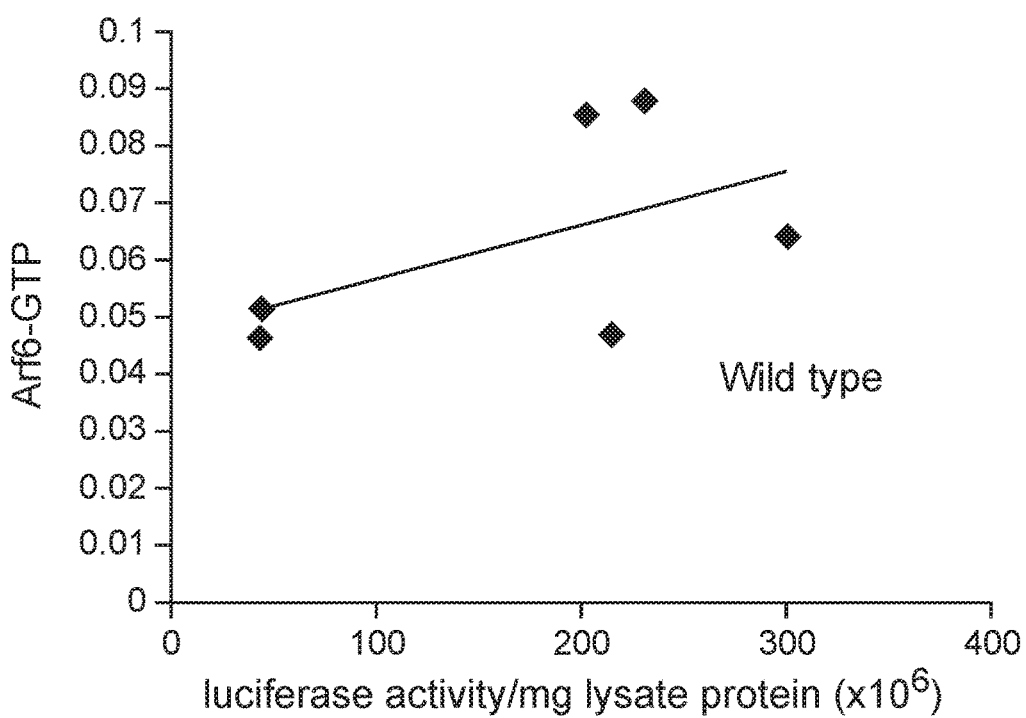

The binding of calmodulin to IQSEC2 has been proposed to regulate IQSEC2 GEF activity for Arf6 promoting Arf6-GTP formation and thereby activating Arf6 (Shoubridge et al, 2010; Myers et al, 2012; Brown et al, 2016). Moreover, a R359C IQSEC2 mutation in the IQ calmodulin binding region of IQSEC2 has been associated with changes in IQSEC2 GEF activity for Arf6 (Shoubridge et al, 2010). Having demonstrated that the A350V affects the interaction of calmodulin for IQSEC2 it was assessed how the A350V mutation may affect the ability of IQSEC2 to promote Arf6-GTP. Arf6-GTP levels by ELISA were assessed in multiple stable transformants of HEK293T expressing different amounts of either wild type or A350V IQSEC2 as assessed by luciferase activity. It was found, using equivalent amounts of protein extract, there was an approximately 25% increase in total Arf6-GTP in HEK293T cells expressing A350V IQSEC2 as compared to wild type IQSEC2 (0.075±0.004 (n=10) vs 0.060±0.015 (n=6); p=0.04). The stable cell lines expressing wild type or A350V IQSEC2 differed markedly in the relative amount of IQSEC2 (as-sessed by luciferase activity) which they produced with overall 5-200 fold more wild type IQSEC2 being produced than mutant IQSEC2 in these cell lines. When normalized for both protein and luciferase activity (i.e. comparing the GEF specific activity of A350V IQSEC2 to wild type IQSEC2) the A350V IQSEC2 protein promoted nearly 30-fold more Arf6-GTP than wild type IQSEC2 protein ($1.6 \times 10^8 \pm 6.8 \times 10^{-9}$ vs. $5.7 \times 10^{-10} \pm 1.7 \times 10^{-10}$, p=0.058). There was a highly significant correlation between the relative amount of A350V IQSEC2 and Arf6-GTP (r=0.77, p=0.009). This correlation was weaker in stable cell lines expressing different amounts of wild type IQSEC2 (r=0.52, p=0.28) (FIGS. 3A and 3B).

Figure 4A:
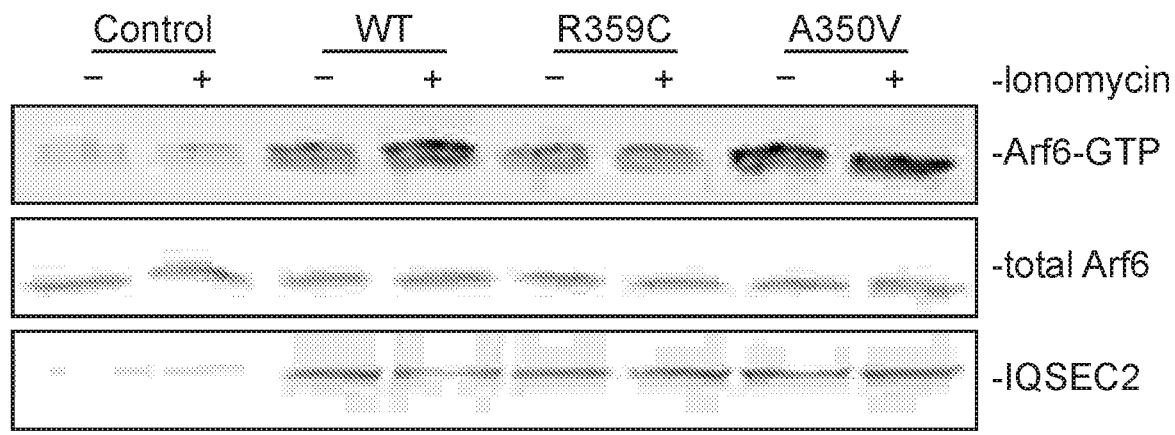
FIG. 4 A-B show that the A350V mutation activates ARF-GEF activity of IQSEC2.
WT, R359C, or A350V IQSEC2 was expressed in HEK293 cells, and treated with either ionomycin or carrier control. Activation of endogenous Arf6 under each condition was assayed in cell lysates by pull-down with GGA3. Precipitates were probed with antibodies against ARF6 (FIG. 4A). Lysates were probed for total Arf6 expression and with antibodies against the FLAG tag on IQSEC2. Arf6-GTP levels are calculated as fold increase over sham-transfected controls and are shown as mean±SD from six independent experiments (FIG. 4B). The GGA pulldown assay was assessed by one-way ANOVA followed by Tukey's Multiple Comparison Test for post hoc analysis. $*p \le 0.01$; $***p \le 0.001$; N.S. Not significant.
Figure 4B:
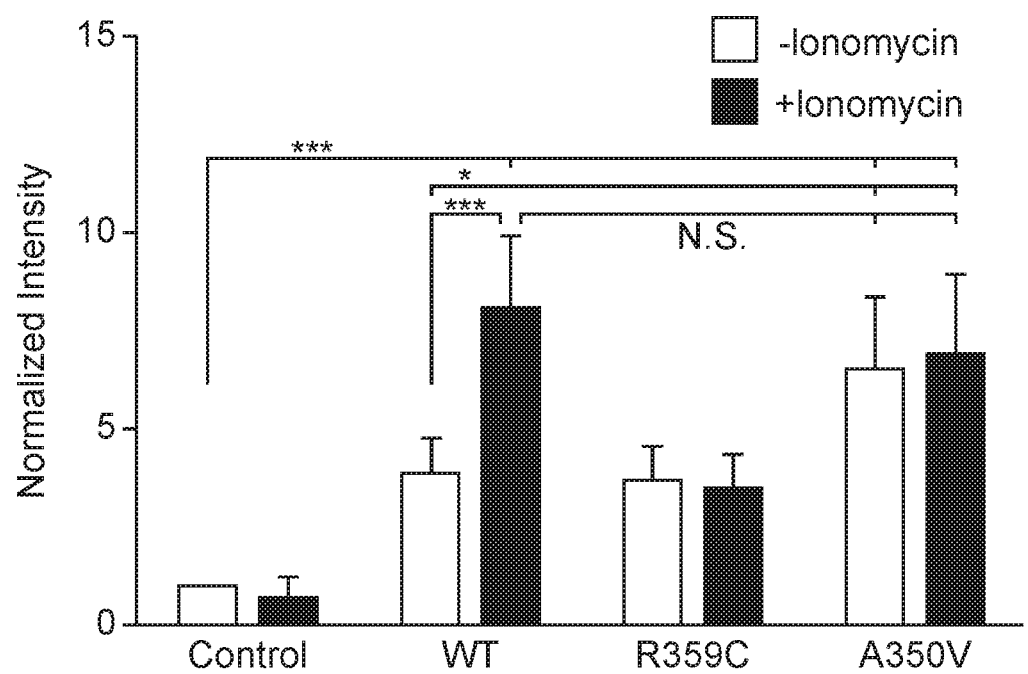

The activation of Arf6 (Arf6-GTP) by wild type, A350V, or R359C IQSEC2 in a GGA3 pulldown assay was also assessed. HEK 293T cells were transiently transfected with constructs to express either wild type, A350V or R359C IQSEC2, and endogenous Arf6 activation was tested with or without treatment with the calcium ionophore ionomycin. Ionomycin has been previously demonstrated to increase IQSEC2 GEF activity and Arf6-GTP formation by stimulating calcium influx and thereby affecting the interaction of calmodulin with IQSEC2 (Myers et al, 2012). Cell lysates were incubated with beads coated with GGA3:GST to isolate the GTP-bound Arfs, and bound Arf6 was assessed by immunoblot (FIG. 4A). Expression of wild type IQSEC2 resulted in 3.87±0.89 fold increase in Arf6 activation compared to sham transfected cells. Ionomycin treatment of cells containing wild type IQSEC2 further doubled Arf6 activation to an 8.03±1.89 fold increase. Transfection with R359C also caused an induction of Arf6-GTP, but this mutant was unresponsive to ionomycin treatment. Transfection of the A350V mutant strongly increased Arf6 activation to a level that was statistically indistinguishable from the cells both transfected with wild type IQSEC2 and treated with ionomycin. In the absence of ionomycin transfection with A350V significantly increased Arf6 activation as compared to wild type (p<0.01) and ionomycin did not further increase Arf6 activation by A350V (FIG. 4B). These data demonstrate that the A350V mutation results in the constitutive activation of IQSEC2 GEF activity for Arf6.

Example 4

Surface AMPA Receptors are Reduced in A350V Hippocampus

Figure 5A:
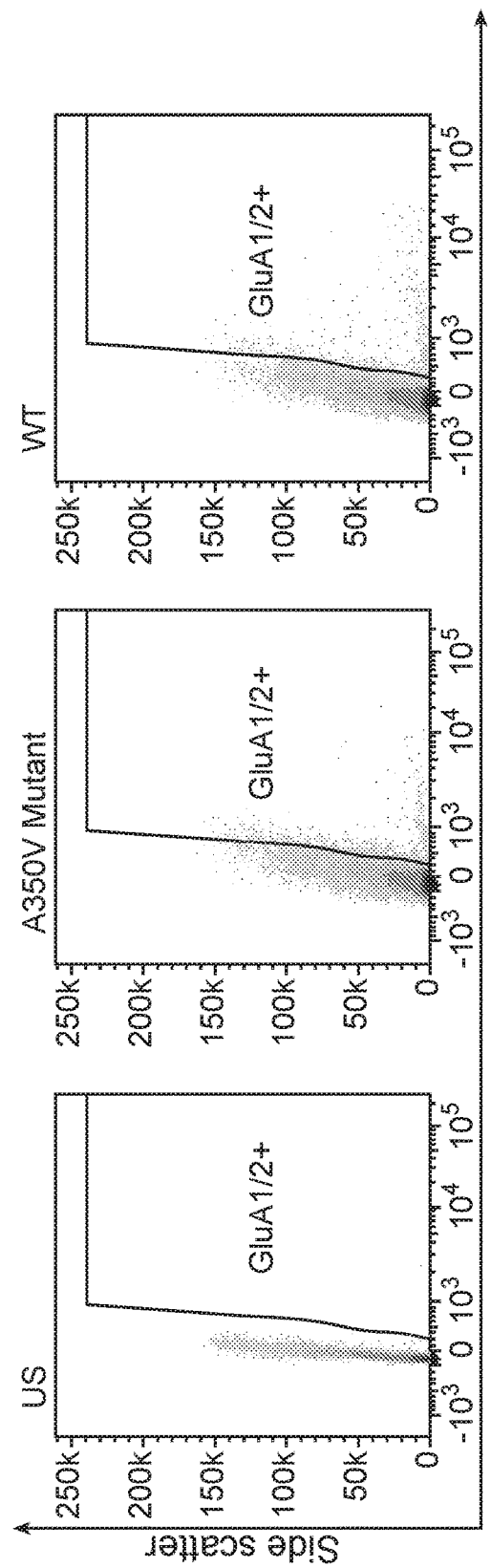
FIG. 5A is representative dot plot of one of 10 experiments. US panel-unstained hippocampal cells. Mut and WT panels demonstrating staining with Alexa Flour 647 for extracellular GluA/2 in single cell suspension of hippocampal cells from A350V and wild type mice respectively and window selected for identifying GluA1/2+ cells. Summary of all experiments (FIG. 5B) demonstrating significantly higher percentage of cells staining with GluA/2 in wild type as compared to A350V mutant hippocampal neuronal preparations (4.1±0.5 vs 3.1±0.5, paired t-test, n=10 independent experiments, p<0.00001).
Figure 5B:
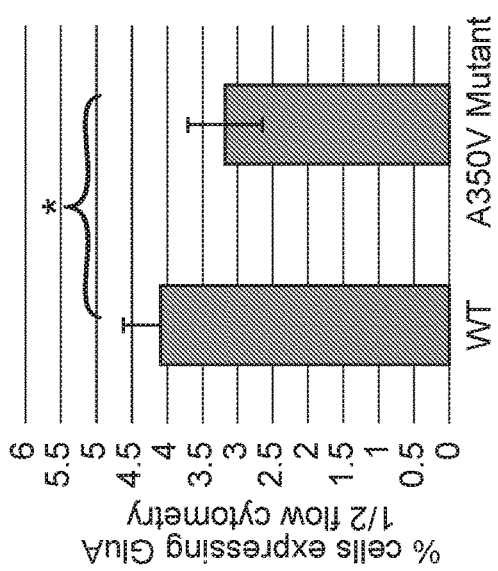
FIG. 5 A-B demonstrate flow cytometry analysis of hippocampal derived cells for GluA1/2
Figures 6A, 6B:
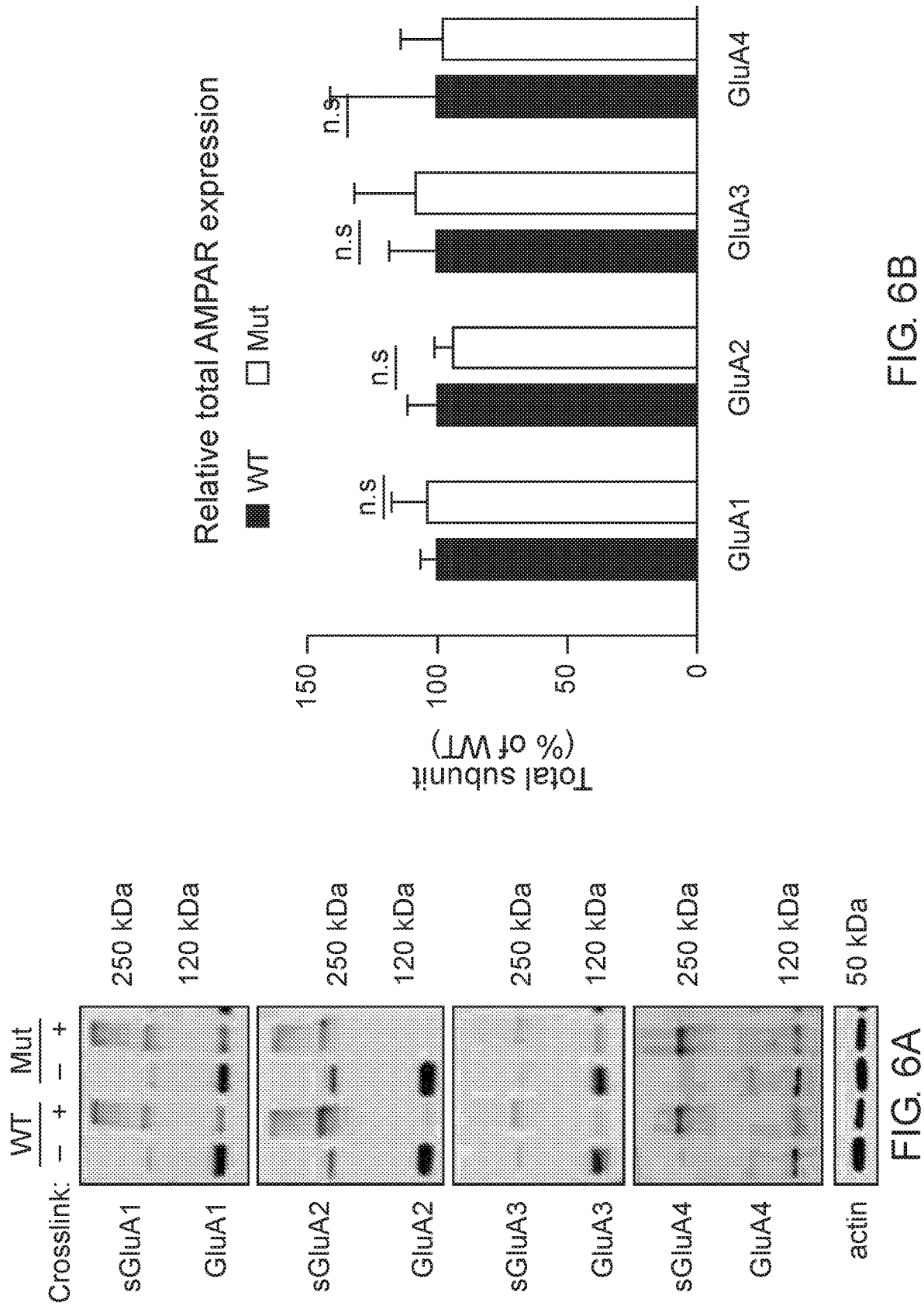
FIGS. 6A-6G. show the assessment of AMPA receptor subunits by surface cross-linking.
Figure 6C:
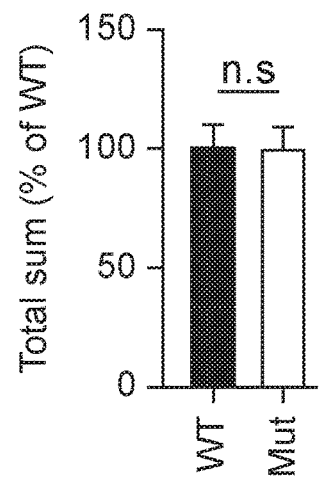
Figure 6D:
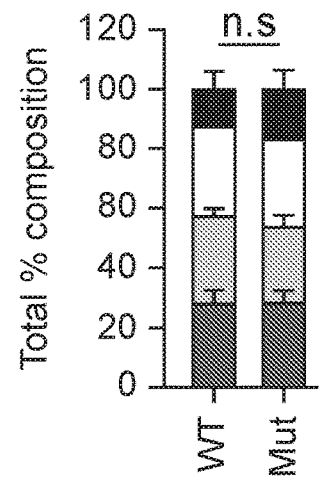
Figure 6E:
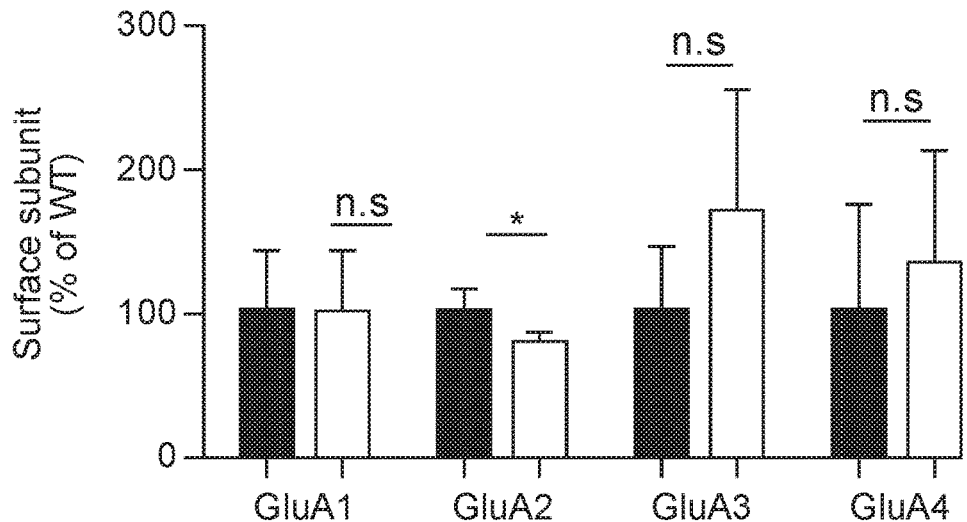
Figure 6F:
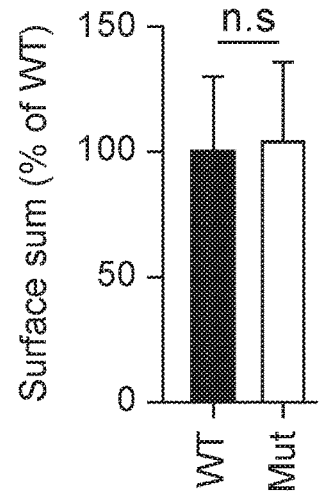
Figure 6G:
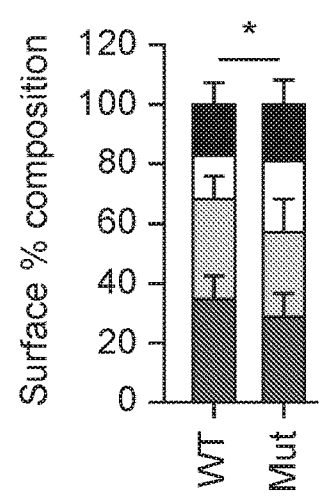

The GEF activity of IQSEC2, mediated through Arf6, has recently been demonstrated to be required for the activity dependent removal of AMPA receptors from the surface of hippocampal neurons (Brown et al, 2016). It was therefore proposed that a constitutive increase in Arf6-GTP by A350V, as was demonstrated in vitro, would result in a down regulation of surface AMPA receptors in hippocampi from A350V IQSEC2 mice as compared to wild type IQSEC2 mice. The expression of total gluA1 and gluA2 receptors in hippocampus and whole brain by western blot from wild type and A350V mice (age 6-8 weeks) was assessed and any difference between the total receptor expression in these mice was found. Accordingly, it was sought to determine if the amount of surface expressed gluA1/2 was different between the wild type and A350V mice. First, by flow cytometry analysis (FIGS. 5A and 5B) gluA1/2 expression on the surface of neurons prepared from hippocampus as described in methods from 6-8 week old male mice was assessed and found a highly significant 30% reduction in the number of cells expressing surface gluA1/2 in A350V as compared to wild type IQSEC2 male mice (mean 4.1%±0.5% vs 3.1%±0.5%; median 3.9% vs 2.7%, n=10 for wild type and mutant mice respectively, paired t-test, $p<0.00001$.) There was also a highly significant reduction in the total amount of gluA1/2 surface expression in those cells identified by flow cytometry as expressing surface gluA1/2 (median difference 51, $p<0.008$ by Wilcoxon signed rank test). Total (intracellular and extracellular) gluA1/2 was not significantly different between wild type and mutant mice assessed by flow cytometry. Second, using a surface cross linking assay coupled with western blot surface AMPA receptors (GluA1-4 subunits) in wild type and mutant hippocampi from male 6-8 week old mice were assessed and it was found that surface expression of GluA2 was significantly reduced in A350V IQSEC2 hippocampus as compared to wild type IQSEC2 hippocampus (FIG. 6) resulting in an overall significant change in the surface distribution of the different AMPA receptor subunits in the A350V mice (unpaired t-test; Two-tailed, t=2.579 df=8, p=0.0327). There was no significant difference between A350V and wild type hippocampus in the amount of total GluA2 AMPA receptor or in the distribution of the total AMPA receptor subunits in these studies. Additionally, immunohistochemistry of surface expression of GluA2 in hippocampus (FIG. 7) further confirmed that GluA2 AMPA receptor surface expression is reduced in A350V male mice compare to control wild type male mice. There was no significant difference in the amount of total GluA2 between A350V and wild type hippocampi as assessed by immunohistochemistry. Collectively, these data demonstrate that hippocampal surface GluA2 is decreased in A350V IQSEC2 mice.

Basal Synaptic Transmission is Decreased in the Hippocampus of A350V IQSEC2 Mice.

In order to determine if the decrease in hippocampal surface AMPA expression was associated with a change in hippocampal synaptic transmission electrophysiological testing using coronal brain slices from A350V and WT IQSEC2 mice as described in methods was performed. Evoked responses were recorded from the dendritic region of hippocampal CA1 pyramidal neurons. An input/output curve representing synaptic responses (fEPSP slope/fiber volley) resulting from different stimulus intensities (FIG. 8). Synaptic responses were significantly lower in A350V IQSEC2 mice as compared to WT IQSEC2 mice. These data demonstrate that basal hippocampal synaptic transmission is decreased in A350V IQSEC2 mice.

Example 5

Behavioral Phenotyping of A350V IQSEC2 Mice

In order to characterize the behavioral phenotype of the A350V IQSEC2 animal model, examined anxiety-like behavior, locomotion, motor coordination, social behavior and learning abilities were conducted. Anxiety-like behavior was assessed in the open field test and no significant difference between A350V male mice (n=13) and WT littermates (n=13) in the time spent in the center of the arena relative to the perimeter (A350V: mean=0.215+/−0.02; WT: mean=0.17+/−0.01, unpaired t-test; t(24)=1.588, p=0.130 was found, suggesting that A350V show normal levels of anxiety-like behavior. Locomotion (total distance traveled) was also assessed using the open field test (FIG. 9A). There was a significant difference between A350V (n=13) and WT littermates (n=13) male mice when measuring the total distance traveled and velocity in the open field arena (unpaired t-test; distance: t(24)=−3.2805, p<0.01; velocity: t(24)=−3.2851, p<0.01). This result was consistent with the increased locomotion found in A350V mice in the habituation phase of the three-chamber social preference test (unpaired t-test; t(24)=2.3125, p<0.05). Motor coordination was assessed in the Rotarod test (FIG. 9B). Both A350V and WT mice performed at similar levels with no significant difference between the two groups in the time spent on the accelerating rotating rod. Social preference of A350V mice towards an unfamiliar conspecific mouse over an inanimate novel object was assessed using a three-chamber social arena (FIG. 9C). Both A350V male mice (n=13) and WT (n=13) littermates preferred to spend more time in close interaction with a social stimulus (Stranger 1) over a novel object (paired t-test; A350V: t(12)=2.535, p<0.05; WT: t(12)=4.671, p<0.001). However, A350V mice showed a trend towards social impairment as measured by a decreased time spent in close interaction with Stranger 1 compared to WT mice (unpaired t-test; t(24)=1.743, p=0.094). Preference for social novelty (FIG. 9D) was assessed by comparing the time spent in close interaction with a novel mouse to an already familiar mouse (Stranger 1). Both A350V (n=9) and WT (n=12) mice preferred an unfamiliar mouse (Stranger 2) relative to a previously encountered mouse (paired t-test; A350V: t(8)=4.367, p<0.01; WT: t(11)=3.134, p<0.01). However, A350V mice spent significantly more time in close interaction with a novel social stimulus (Stranger 2) over the familiar mouse compared to WT mice (unpaired t-test; t(19)=2.294, p<0.05). Hippocampal-dependent memory was assessed using the Morris water maze test (FIG. 9E). Time in the target quadrant during a probe trial was compared between female A350V (n=5) and WT (n=5) mice revealing a significant difference between the groups (Mann-Whitney U-test; U=39.5, p<0.05). Collectively, these data demonstrate that the A350V IQSEC2 mice model manifests some of the abnormalities found in the human index case with the A350V IQSEC2 mutation, specifically hyperactivity, abnormal social interactions and impaired cognitive function.

Example 6

Assessment of a Drug that is an AMPA Receptor Positive Allosteric Modulator in the Animal Model of the Invention A mouse model and IPS (stem cell model) of autism, intellectual disability and epilepsy based on a human mutation in the IQSEC2 gene (Alanine for Valine substitution at amino acid residue 350) was used in this experiment. The mice were created by CRISPR with this mutation recapitulate the phenotype seen in man with increased epilepsy, ID, and autistic like features. Further, induced pluripotent stem cells from the child with the mutation and neurons from these cells were used. Both models are believed to be a platform for drug development.

The mechanism by which the A350V mutation results in intellectual disability and autism appears to be related to a down regulation of AMPA receptors. These receptors have been implicated in learning and memory and social behavior. It was therefore proposed that increasing AMPA receptors in the brain will provide clinical benefit. The drug initially made by Pfizer (PF-04958242) and then purchased by Biogen (BIIB 104) is a first in class AMPA receptor positive allosteric modulator which is now in phase 2 clinical studies for treating intellectual disability. This drug is now under investigation to assess the ability of this drug to correct the deficiency in AMPA receptors in the A350V model and thereby provide clinical benefit. Specifically, the ability of the drug to increase AMPAR expression in the brain and to improve the learning, memory and social behavioral defects seen in A350V mice is now assessed and it is believed that the drug will be beneficial in this animal model and hence is a good candidate for treating a patient having a mutation in the mutation in the IQ domain of IQSEC2 and in particular an A350V mutation.

Example 7

Use of the A350V Platforms (Mice and Stem Cells) for Identifying Drug for Treating Epilepsy These A350V platforms (mice and stem cells) will be useful also for assessing and developing candidate drugs for treating epilepsy. The A350V mice have seizures and the IPSC derived neurons from the child with the mutation displays electrophysiological features consistent with epilepsy making this an ideal platform to check new drugs that can prevent epilepsy. Over 30% of all cases of epilepsy are drug resistant and this A350V model will provide a new venue and mechanism of action on which drugs may be assessed to prevent seizures.

Example 8

Use of IPSCs Having A350V Mutation and IPSCs in which the Mutation is Corrected to A350A for Identifying Drug for Treating Epilepsy Induced pluripotent stem cell technology allows one to create a human disease model from patients in which one can study basic cellular processes involved in the disease and use as a platform for drug therapy. The procedure involves (with Human Subjects approval) taking a small piece of skin and growing fibroblasts from this skin. The fibroblasts are then transfected with four genes that have been shown to return the fibroblasts to a pluripotent state (stem cell) from which they may be differentiated into any cell type depending on the growth conditions used to culture the stem cells. An important aspect of this approach to study human disease is that the stem cells themselves can be genetically modified to remove the disease-causing mutation (reverting the DNA sequence of relevance to the normal sequence) thereby allowing one by comparison of the parent cells and corrected cells to know what differences are actually due to the mutation. This helps one guide and select targets for drug therapy. In one embodiment of the invention, the stem cells so derived from the fibroblasts (and corrected using CRISPR technology) can then be differentiated into neurons using specific growth factors. This can be done using fibroblasts taken from the child with the A350V mutation (with institutional approval and parental consent) and have studied the biology of the neurons differentiated from the stem cells produced from this child as well as the corrected stem cells. Functional differences between the cells of the child and the corrected cells in their electrophysiological properties (decreased basal synaptic transmission) similar to what those described in the A350V mice. In addition, early on the development of these cells that shown to have an increased propensity to undergo repetitive depolarizations similar to what one would see in epilepsy making them a good source for studying epilepsy. An additional finding in these cells is that the neuronal cultures derived from these cells are deficient in the production of cells producing the neurotransmitter GABA-producing an inhibitory excitatory imbalance and possibly explaining the increased epilepsy inpatients with A350V. This would also suggest that GABA replacement therapy may be efficacious in preventing these seizures.

The stem cell derived neuronal cultures may therefore be used to study processes that mimic epilepsy, that mimic changes in the trafficking of membrane receptors that we see in vivo in the mice model and to serve as a platform for drug discovery. Another emerging use of the neurons derived from the stem cells is the development of organoid structures-in vitro developed cell cultures in which cells develop into a network of interconnecting neurons which communicate with one another and may actually mimic properties of brain tissue as opposed to isolated cells. These organoids also derived from A350V may be used for drug development as well.

Currently using the cell culture model AMPA receptor trafficking, production of GABAergic neurons and ARF6 activation are assessed as targets for drug therapy. Costs of working in vitro with the stem cells is much less than working in the mice and allows a more rapid throughput system for screening drugs. Thus, the invention further provides two types of IPSCs-those directly from the child with the A350V mutation and then the mutation is corrected to produce A350A (changing the V back to an A). This allows us to say that differences seen between the two IPSCs is due to differences in IQSEC2.

Summary and Discussion of the Results

This study provides new findings for understanding the regulation of IQSEC2 activity and the pathophysiology of a new IQSEC2 mutant (A350V) with implications for drug therapy. First, it was demonstrated that calcium increases the binding of IQSEC2 to calmodulin and the data with previously reported conflicting results. Second, the first mutation identified in humans associated with a constitutive activation of Arf6 due to a constitutive increase in IQSEC2 GEF activity was reported Third, it was demonstrated that surface GluA2 AMPA receptors are decreased in the brains of A350V IQSEC2 mice. Finally, it was demonstrated that A350V IQSEC2 mice have abnormal behavioral phenotypes with increased locomotion, abnormal social interactions and decreased learning.

It was demonstrated in two different systems, in vitro with cell extracts and in cells, that apocalmodulin can bind to IQSEC2 and that this binding is impaired with the A350V mutant. In a resting cell (i.e., HEK 293T cells, neurons) the cytoplasmic concentration of free calcium is 50-100 nM (Persechini and Cronk et al, 1999) with localized calcium concentrations of 1-10 μM being achieved with an appropriate stimulus (i.e. NMDA receptor activation in neurons). The $K_d$ of calcium for calmodulin is approximately 1 μM with essentially no calcium calmodulin being found in a cell with a free cytoplasmic calcium of less than 200 nM (Persechini and Cronk et al, 1999). The demonstration that half-maximal interaction between calmodulin and IQSEC2 occurs at around 1 μM calcium is therefore physiologically relevant.

However, while A350V binds less efficiently to apocalmodulin as compared to wild type IQSEC2, the A350V mutant is capable of binding calcium-calmodulin equivalent to or even superior to wild type IQSEC2. Similar to myosin (Trybus et al, 2007) the epitope or conformation within the IQ region of IQSEC2 recognized by apocalmodulin and calcium calmodulin may be different. The finding that A350V IQSEC2 can effectively bind to calcium-calmodulin but not apocalmodulin may suggest that the alpha helical distortion of the IQ domain in the A350V IQSEC2 mutant induced by the valine-for-alanine substitution introduces a change in the conformation of the IQ motif of IQSEC2 that is similar to the conformation of the IQ motif that is induced in wild type IQSEC2 by the binding of calcium calmodulin. The wild type IQSEC2 IQ motif may adopt a relaxed conformation in which apocalmodulin may bind when calcium-calmodulin is not present; however, in the A350V mutation the conformation of the IQ region may be locked in a conformation which will not allow it to assume a conformation permissive for apocalmodulin binding.

This is the first demonstration of a human disease resulting from a constitutive activation of Arf6 due to a constitutive increase in IQSEC2 GEF activity. It was shown that the IQSEC2 GEF activity for Arf6 is increased in cells expressing mutant A350V IQSEC2 as compared to wild type IQSEC2. Ionomycin treatment of cells expressing WT IQSEC2 induced a significant increase in Arf6 activation, indicating a calcium-dependent regulation of Arf-GEF activity. The A350V mutant, however, already had a high level of basal activity that was comparable to WT IQSEC2 after treatment with ionomycin. All previously reported mutants of IQSEC2, including R359C, which is also located in the IQ region, have been noted to have decreased Arf6 GEF activity (Shoubridge et al, 2010). It was also shown that the GEF activity of the R359C mutant is not elevated by ionomycin treatment, which suggests that deficits in calcium dependent regulation of this mutant may contribute to ID. It is proposed that the constitutive activation of IQSEC2 GEF activity by the A350V mutation may be due to the mutation locking the IQ motif into the same conformation as wild type IQSEC2 bound to calcium-calmodulin (wherein IQSEC2 GEF activity is increased).

A key factor underlying the strength of individual excitatory synapses is the number of AMPA receptors at synapses. Trafficking of AMPA receptors to and from synapses plays a key role in synaptic transmission and in experience-dependent synaptic plasticity and associative learning (Qin et al, 2005; Rumpel et al, 2005; McCormack et al, 2006; Hu et al, 2007; Matsu et al, 2008; Kielland et al, 2009; Zhu, 2009). NMDA receptor-induced removal of GluA1/2 AMPA receptors from synapses is a key step in the induction of long-term depression (LTD), and Arf6 activation is a necessary component of this type of plasticity (Brown et al, 2016; Scholz et al, 2010). IQSEC2 regulates AMPA receptor currents (Myers et al, 2012; Brown et al, 2016). The Arf-GEF activity of IQSEC2 is required for LTD, as ID-linked mutations in IQSEC2 that decrease its Arf-GEF activity impair its induction (Brown et al, 2016). This indicates that properly regulated activation of Arf6 by IQSEC2 is necessary for normal synaptic plasticity processes, including the regulated removal of AMPA receptors in LTD. The findings here showing that increased Arf6 activity is associated with decreased GluA2 AMPA surface expression in A350V mutant brain tissue is consistent with the critical role of Arf6 in regulating the removal of AMPA receptors from the plasma membrane (Brown et al, 2016). The demonstration that basal hippocampal synaptic transmission is decreased in A350V IQSEC2 mice is also consistent with a down-regulation of AMPA receptors in this model.

Based on the data presented here and previous work presented by others (Myers et al, 2012; Brown et al, 2016) FIG. 10 shows a model for the activation of wild type IQSEC2 by calcium as well as the pathophysiological consequences of the A350V IQSEC2 mutation. In the presence of wild type IQSEC2, the binding of glutamate to the NMDA receptor leads to calcium influx and a rise in free intracellular calcium. This calcium binds to calmodulin and the binding of calcium calmodulin to the IQ site on IQSEC2 induces the GEF activity of IQSEC2 allowing it to promote the formation of Arf6-GTP. Arf6-GTP, in turn, regulates endocytosis of surface AMPA receptors by pathways that are poorly understood, but which may include JNK (Myers et al, 2012). On the other hand, in the A350V IQSEC2 mutant, IQSEC2 GEF activity for Arf6 is constitutively activated resulting in persistently increased Arf6 activity, which may markedly downregulate surface AMPA receptors, specifically GluA2, (representing an exaggerated form of long-term depression). Thus, the normal processes for regulating AMPA receptor levels at synapses are compromised by the A350V IQSEC2 mutation. This hypothesis appears to provide a mechanistic basis for the defects in behavior and learning associated with the A350V IQSEC2 mutation. Furthermore, according to this hypothesis, treatment to restore the balance in AMPA transmission by blocking exaggerated AMPA downregulation may provide clinical benefit specifically an increase in learning potential. The size of the change in surface GluA2 AMPA induced by the A350V mutation is similar to what has been reported in mutations in the Thorase gene (Piard et al, 2018; Umanah et al 2017) where pharmacological attempts to restore normal surface AMPA activity have shown therapeutic benefit in man (Ahrens et al, 2017).

Behavioral phenotyping of the A350V IQSEC2 mice demonstrates increased locomotion, abnormal social interactions and learning impairments in the absence of motor coordination deficits. The increased preference for social novelty in the A350V mice described here, while different from what has been described in autism, has been described in other genetic encephalopathies with intellectual disability and abnormal social functioning such as Williams's syndrome (Martin et al, 2018; Ng et al, 2018). The behavioral findings in the A350V mice appear to model to some of the abnormal behaviors found in the human index case with the A350V mutation, specifically hyperactivity, abnormal social interactions with no inhibitions with strangers and impaired cognitive function. However, more complete behavioral phenotyping of the A350V IQSEC2 model will be required in order to properly define the spectrum of social interaction abnormalities, hyperactivity features, and the type of learning and memory impairment present in these mice. Decreases in surface AMPA receptors have been noted in other models of learning impairment (neurodevelopmental as well as Alzheimer's disease) and in models of social dysfunction (Ahrens et al, 2017; Piard et al, 2018; Umanah et al, 2017; Guntupalli et al, 2016; Tian et al, 2018; Kim et al, 2018) and increasing AMPA transmission has shown benefit in these models (Lauterborn et al 2016; Kim et al, 2018). Accordingly, strategies designed to restore surface AMPA in the A350V IQSEC2 mouse model may have a beneficial effect on cognitive and affective behavior and represents a potential actionable node for treatment in humans for the A350V IQSEC2 mutation.

REFERENCES

Ahrens-Nicklaus, R. C., Umanah, G. K. E., Sondheim, N., Deardorff, M. A. Wilkens A. B., Conlin, L. K., et al (2017). Precision therapy for a new disorder of AMPA receptor recycling due to mutations in ATAD1. Neurol Genet 2017; 3: e130. doi:10.1212/NXG.0000000000000130

Alexander-Bloch, A., McDougle, C., Ullman, Z., Sweetser, D. (2016). IQSEC2 and X-linked syndromal intellectual disability. Psychiatric Genetics 26, 101-108. doi: 10.1087/YPG.0000000000000128

Awasthi, A., Ramachandran, B., Ahmed, S., Benito, E., Shinoda, Y., Nitzan, N., et al. (2018) Synaptotagmin-3 drives AMPA receptor endocytosis, depression of synapse strength, and forgetting. Science doi: 10.1126/science.aac1483

Bahler, M., Rhoads, A. (2002) Calmodulin signaling via the IQ motif. FEBS Letters 513, 107-113

Brown, J. C., Petersen, A., Zhong, L., Himelright, M. L., Murphy, J. A., Walikonis, R. S., et al. (2016) Bidirectional regulation of synaptic transmission by BRAG1/IQSEC2 and its requirement in long-term depression. Nature Comm. 7, 11080. doi:10.1038/ncomms11080

Choi S, Ko J, Lee J R, Lee H W, Kim K, Chung H S et al (2006). ARF6 and EFA6A regulate the development and maintenance of dendrites. J Neurosci 26: 4811-4819. doi:10.1523/JNEUROSCI.4182-05.2006

Donaldson J G. Multiple roles for Arf6: sorting, structuring and signaling in the plasma membrane (2003). J Biol Chem 278: 41573-6. doi: 10:1074/jbc.R300026200

Fieremans, N., Van Esch, H., de Ravel, T., Van Driessche, J., Belet, S., Bauters, M., et al. (2015). Microdeletion of the escape genes KDM5C and IQSEC2 in a girl with severe intellectual disability and autistic features. Eur. J. Med. Genet. 58, 324-327. doi: 10.1016/j.ejmg.2015.03.003

Guntupalli, S., Widagdo, J., Anggono, V. Amyloid B induced dysregulation of AMPA receptor trafficking. Neur Plast 2016; doi: 10.1155/2016/3204519

Heyne, H. O., Singh, T., Stamberger, H., Jamra, R. A., Caglayan, H., Craiu, D., et al (2018). De novo variants in neurodevelopmental disorders with epilepsy. Nat Genet 50, 1048-1053. doi: 10.1038/s41588-018-0143-7.

Hinze, S. J., Jackson, M. R., Lie, S., Jolly, L., Field, M., Barry, S. C., et al. (2017) Incorrect dosage of IQSEC2, a known intellectual disability and epilepsy gene, disrupts dendritic spine morphogenesis. Transl. Psych. 7, e1110. doi: 10.1038/tp.2017.81

Hu, H., Real, E., Takamiya, K., Kang, M. G., Ledoux, J., Huganir, R. L., Malinow, R. (2007) Emotion enhances learning via norepinephrine regulation of AMPA receptor trafficking. Cell 131, 160-173. doi: 10.1016/j.cell.2007.09.017

Jaworski, J. (2007) ARF6 in the nervous system. Eur J Cell Biol 86: 513-524; doi: 10.1016/j.ejcb.2007.04.007

Kalscheuer, V. M., James, V. M., Himelright, M. L., Long, P., Oegema, R., Jensen, C., et al. (2016) Novel missense mutation A789V in IQSEC2 underlies X-linked intellectual disability in the MRX78 family. Front. Mol. Neuro. 8, 85. doi: 10.3389/fnmol.2015.00085

Karl T, Pabst R, Von Horsten S (2003). Behavioral phenotyping of mice in pharmacological and toxicological research. Experimental and Toxicologic Pathology 55: 69-83.

Kielland, A., Bochorishvilli, G., Corson, J., Zhang L., Rosin D. L., Heggelund P., et al. (2009) Activity patterns govern synapse specific AMPA-R trafficking between deliverable and synaptic pools. Neuron 62, 84-101. doi: 10.1016/j.neuron.2009.03.001

Kim, J. W., Park, K., Kang, R. J., Gonzales, E. L. T., Kim, D. G., Oh, H. A., et al. (2018). Pharmacological modulation of AMPA receptor rescues social impairments in animal models of autism. Neuropsychopharmacology doi: 10.1038/s41386-018-0098-5.

Lauterborn J C, Palmer L C, Jia Y, Pham D T, Hou B, Wang W, et al (2016) Chronic Ampakine Treatments Stimulate Dendritic Growth and Promote Learning in Middle-Aged Rats. J Neurosci 36:1636-1646.

Martin, L. A., Iceberg, E., Allaf, G. (2018). Consistent hypersocial behavior in mice carrying a deletion of Gtf2i but no evidence of hyposocial behavior with Gtf2i duplication: implications for Williams-beuren syndrome and autism spectrum disorder. Brain Beh 8: e00895; doi: 10.1002/brb3.895

Matsu, N., Reijmers, L., Mayford, M. (2008). Spine type specific recruitment of newly synthesized AMPA receptors with learning. Science 319, 1104-1107. doi: 10.1126/science.1149967

McCormack, S. G., Stronetta, R. L., Zhu, J. J. (2006). Synaptic AMPA receptor exchange maintains bidirectional plasticity. Neuron 50, 75-88. doi: 10.1016/jneuron.2006.02.027

Medin, T., Jensen, V., Skare, O., Storm-Mathisen, J., Hvalby, O., Bergersen, L. H. (2018). Altered a-amino-3-hydroxy-5-methyl-4-isoxazolepropionic acid (AMPA) receptor function and expression in hippocampus in a rat model of attention-deficit/hyperactivity disorder (ADHD). Behav Brain Res 360: 209-215.

Mignot, C., Depienne, C. (2018). IQSEC2 related encephalopathy in males and females: a comparative study including 37 novel patients. Genet in Medicine doi:10.1038/s41436-018-0268-1.

Moy, S. S., Nadler, J. J., Perez, A., Barbaro, R. P., Johns, J. M, Magnuson, T. R., et al (2004). Sociability and preference for social novelty in five inbred strains: an approach to assess autistic-like behavior in mice. Genes Brain Behav. 3, 287-302. doi: 10.1111/j.1601-1848.2004.00076.x Murphy, J. A., Jense, O. N., Walikonis, R. S. (2006) BRAG1 a Sec7 domain containing protein is a component of the postsynaptic density of excitatory synapses. Brain Res. 1120, 35-45. doi:10.1016/j.brainres.2006.08.096

Myers, K. R., Wang, G., Sheng, Y., Conger, K. K., Casanova, J. E., Zhu, J. J. (2012) Arf6-GEF BRAG1 regulates JNK-mediated synaptic removal of GluA1-containing AMPA receptors: a new mechanism for nonsyndromic X-linked mental disorder. *J. Neurosci.* 32, 11716-11726. doi: 10.1523/JNEUROSCI.1942-12.2012

Ng, P. R., Bellugi, E. U., Trauner, M. D. (2018) Associations between social functioning, ADHD symptomatology, and emotion functioning in children with autism spectrum disorder and Williams syndrome. *Ped Neur* 79: 69-71. Doi: 10.1016/j.pediatrneurol.2017.10.022\

Parkinson, G. T., Hanley, J. G. (2018). Mechanisms of AMPA receptor endosomal sorting. *Front Mol Neurosci*; doi:10.3389/fnmol.2018.00440

Persechini, A., Cronk, B. (1999). The relationship between the free concentrations of Ca2+ and Ca2+-calmodulin in intact cells. *J. Biol. Chem.* 274, 6827-6830. doi: 10.1074/jbc.274.11.6827

Petersen, A., Brown, J. C., Gerges, N. Z. (2018). BRAG1/IQSEC2 as a regulator of small GTPase-dependent trafficking. *Small GTPases*; doi:10.1080/21541248.2017.1361898

Piard, J., Umanah, G. K. E., Harms, F. L., Abaide-Atristain, L., Amram, D., Chang, M., et al (2018). A homozygous ATAD1 mutation impairs postsynaptic AMPA receptor trafficking and causes a lethal encephalopathy. *Brain* 141, 651-661. doi: 10.1093/brain/awx377

Prut L, Belzung C. (2003). The open field as a paradigm to measure the effects of drugs on anxiety like behaviors: a review. *Eur J Pharm* 463: 3-33.

Qin, Y., Zhu, Y., Baumgart, J. P., Stornetta, R. L., Seidenman K., Mack V., et al. (2005) State dependent Ras signaling and AMPA receptor trafficking. *Genes Dev.* 19, 2000-2015. doi: 10.1101/gad.342205

Rumpel, S., LeDoux, J., Zador, A., Malinow, R. (2005). Post synaptic receptor trafficking underlying a form of associative learning. *Science* 308, 83-88. doi: 10.1126/science.1103944

Sakagami, H., Sanda, M., Fukaya, M., Miyazaki, T., Sukegawa, J., Yanagisawa, T., et al. (2008) IQ-ArfGEF/BRAG1 is a guanine nucleotide exchange factor for ARF6 that interacts with PSD-95 at post-synaptic density of excitatory synapses. *Neuro. Res.* 60, 199-212. doi: 10.1016/j.neures.2007.10.013

Scholz, R., Berberich, S., Rathgeber, L., Kolleker, A., Kohr, G., Kornau, H. C. (2010) AMPA receptor signaling through BRAG2 and Arf6 critical for long term synaptic depression. *Neuron.* 66, 768-780. doi: 10.1016/j.neuron.2010.05.003

Shoubridge, C., Tarpey, P. S., Abidi, F., Ramsden, S. L., Rujirabenjerd, S., J. A. Murphy, et al. (2010). Mutations in the guanine nucleotide exchange factor gene IQSEC2 cause nonsyndromic intellectual disability. *Nat Genet* 42, 486-488. doi: 10.1038/ng.588

Shoubridge, C., Harvey, R. J., Dudding-Byth, T. (2019). IQSEC2 mutation update and review of the female-specific phenotype spectrum including intellectual disability and epilepsy. *Human Mutation* 2019; 40: 5-24.

Singh, S. K., Kishore, N. (2006). Thermodynamic insights into the binding of Triton X-100 to globular proteins: A colorimetric and spectroscopic investigation. J Phys Chem 110, 9728-9737. Doi: 10.1021/jp0608426.

Tian C, Kay Y, Sadybekov A, Rao S, Katritch V, and Herring B E (2018). An intellectual disability-related missense mutation in Rac1 prevents LTP induction. *Front Mol Neuro* 11: 223. Doi: 10.3389/fnmol.2018.00223

Taipale, M., Krykbaeva, I., Koeva, M., Kayatekin, C., Westover, K. D., Karras, G. I., et al. (2012). Quantitative analysis of hsp90-client interactions reveals principles of substrate recognition. *Cell.* 150, 987-1001. doi: 10.1016/j.cell.2012.06.047

Trybus, K. M., Gushchin, M. I., Lui, H., Hazelwood, L., Krementsova, E. B., Volkman, N., et al. (2007) Effect of calcium on calmodulin bound to the IQ motifs of Myosin V. *J. Biol. Chem.* 282, 23316-23325. doi:10.1074/jbc.M701636200

Umanah, G. K. E., Pignatelli, M., Yin, X., Chen, R., Crawford, J., Neifert, S., et al (2017) Thorase variants are associated with defects in glutamatergic neurotransmission that can be rescued by Perampanel. *Sci Transl Med* 9, eaah4985. doi: 10.1126/scitranslmed.aah4985

Vorhees C V and Williams M T. (2006). Morris water maze procedures for assessing spatial and related forms of learning and memory. *Nature protocols* 1: 848.

Wang, X., Putkey, J. A. PEP-19 modulates calcium binding to calmodulin by electrostatic steering. (2016). *Nature communications* 7:13583; doi: 10.1038/ncomms13583.

Yang, X., Boehm, J. S., Yang, X., Salehi-Ashtiani, K., Hao, T., Shen, Y., et al. (2011). A public genome-scale lentiviral expression library of human ORFs. *Nat. Methods* 8, 659-661. doi: 10.1038/nmeth.1638

Zerem, A., Haginoya, K., Lev, D., Blumkin, L., Kivity, S., Linder, I., et al. (2016). The molecular and phenotypic spectrum of IQSEC2-related epilepsy. *Epilepsia* 57, 1858-1869. doi: 10.1111/epi.13560

Zipper, R., Baine, S. D., Genizi, J., Maoz, H., Levy, N. S., Levy A. P. (2017). Developmental progression of intellectual disability, autism and epilepsy in a child with an IQSEC2 gene mutation. *Clinical Case Reports* in press. doi:10.1002/ccr3.1139

Zhu, J. J. (2009). Activity dependent synapse specific AMPA receptor trafficking regulates transmission kinetics. *J Neurosci* 29, 6320-6335. doi: 10.1523/JNEUROSC.4630-08.2009

What is claimed is:

1. A method of screening for a potential candidate for treating autism; and/or intellectual disability associated with an A350V mutation in the IQ domain of IQSEC2 in a subject in need thereof, the method comprising:
   contacting a cell culture model or an animal model having an A350V mutation in the IQ domain of IQSEC2 with a potential drug; and
   detecting increased surface expression of GluA2 AMPA receptors in the animal brain or in the cell,
   wherein if the potential drug is capable of
      increasing the surface expression of GluA2 AMPA receptors in the animal brain or in the cell,
      the potential drug is determined to be a potential candidate suitable for treating autism and/or intellectual disability in a subject.

2. The method of claim 1, wherein the increasing the surface expression of GluA2 AMPA receptors in the brain is in the hippocampal tissue.

3. The method of claim 1, wherein the animal model is a CRISPR murine model.

4. The method of claim 1, wherein the cell culture model is induced pluripotent stem cells (IPS).

* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: artificial sequence
<220> FEATURE:
<223> OTHER INFORMATION: Synthetic Sequence

<400> SEQUENCE: 1
ggcagccctg cggctcagga                                                   20

<210> SEQ ID NO 2
```

```
<211> LENGTH: 90
<212> TYPE: DNA
<213> ORGANISM: artificial sequence
<220> FEATURE:
<223> OTHER INFORMATION: Synthetic Sequence

<400> SEQUENCE: 2
ctgagctgcg cagccgctca aagttcttat tcatacggta ctgtcgaaag gctgtctgga      60
tggtcctggc aacacggcgg ctcaggaagg                                      90
```